(12) United States Patent
Videbaek et al.

(10) Patent No.: US 10,172,594 B2
(45) Date of Patent: *Jan. 8, 2019

(54) TISSUE HANDLING SYSTEM WITH REDUCED OPERATOR EXPOSURE

(71) Applicant: Bard Peripheral Vascular, Inc., Tempe, AZ (US)

(72) Inventors: Karsten Videbaek, Jyllinge (DK); Lasse G. Staal, Jyllinge (DK); Tomas Gundberg, Viby Sjaelland (DK); Lasse Danborg, Glostrup (DK)

(73) Assignee: Bard Peripheral Vascular, Inc., Tempe, AZ (US)

( * ) Notice: Subject to any disclaimer, the term of this patent is extended or adjusted under 35 U.S.C. 154(b) by 60 days.

This patent is subject to a terminal disclaimer.

(21) Appl. No.: 15/407,302

(22) Filed: Jan. 17, 2017

(65) Prior Publication Data
US 2017/0181732 A1  Jun. 29, 2017

Related U.S. Application Data

(63) Continuation of application No. 14/514,660, filed on Oct. 15, 2014, now Pat. No. 9,566,045, which is a continuation of application No. 13/931,116, filed on Jun. 28, 2013, now abandoned, which is a continuation of application No. 12/444,084, filed as
(Continued)

(51) Int. Cl.
*A61B 5/00* (2006.01)
*A61B 10/00* (2006.01)
*A61B 10/02* (2006.01)
*B01L 3/00* (2006.01)

(52) U.S. Cl.
CPC ...... *A61B 10/0096* (2013.01); *A61B 10/0266* (2013.01); *A61B 10/0275* (2013.01); *B01L 3/502* (2013.01); *B01L 3/523* (2013.01); *A61B 2010/0225* (2013.01); *B01L 2200/026* (2013.01); *B01L 2200/0621* (2013.01); *B01L 2200/141* (2013.01); *B01L 2300/049* (2013.01); *B01L 2300/087* (2013.01);
(Continued)

(58) Field of Classification Search
CPC . A61B 10/02; A61B 10/0266; A61B 10/0275; A61B 10/0096; A61B 2010/0225; A61B 2017/320064
See application file for complete search history.

(56) References Cited

U.S. PATENT DOCUMENTS

| 737,293 A | 8/1903 | Summerfeldt |
| 1,585,934 A | 5/1926 | Muir |

(Continued)

FOREIGN PATENT DOCUMENTS

| CN | 101011268 A | 8/2007 |
| CN | 101032420 A | 9/2007 |

(Continued)

*Primary Examiner* — Max Hindenburg

(57) ABSTRACT

A tissue handling system includes a biopsy device configured to deliver at least one tissue sample to a location outside the body of a patient. A tissue storage container is separate from the biopsy device. A tissue collecting device is configured to releasably engage the biopsy device to receive the at least one tissue sample from the biopsy device. The tissue collecting device is configured to be disengaged from the biopsy device and engaged with the tissue storage container to deliver the at least one tissue sample to the tissue storage container.

13 Claims, 16 Drawing Sheets

Related U.S. Application Data application No. PCT/EP2007/060615 on Oct. 5, 2007, now Pat. No. 8,485,987.

(60) Provisional application No. 60/850,004, filed on Oct. 6, 2006.

(52) U.S. Cl.
CPC .............. B01L 2300/0832 (2013.01); B01L 2400/0457 (2013.01); B01L 2400/0644 (2013.01)

(56) References Cited

U.S. PATENT DOCUMENTS

| | | |
|---|---|---|
| 1,663,761 A | 3/1928 | Johnson |
| 2,953,934 A | 9/1960 | Sundt |
| 3,019,733 A | 2/1962 | Braid |
| 3,224,434 A | 12/1965 | Molomut et al. |
| 3,289,669 A | 12/1966 | Dwyer et al. |
| 3,477,423 A | 11/1969 | Griffith |
| 3,512,519 A | 5/1970 | Hall |
| 3,561,429 A | 2/1971 | Jewett et al. |
| 3,565,074 A | 2/1971 | Foti |
| 3,606,878 A | 9/1971 | Kellogg |
| 3,727,602 A | 4/1973 | Hyden et al. |
| 3,732,858 A | 5/1973 | Banko |
| 3,785,380 A | 1/1974 | Brumfield |
| 3,800,783 A | 4/1974 | Jamshidi |
| 3,844,272 A | 10/1974 | Banko |
| 3,882,849 A | 5/1975 | Jamshidi |
| 3,889,682 A | 6/1975 | Denis et al. |
| 3,916,948 A | 11/1975 | Benjamin |
| 4,275,730 A | 6/1981 | Hussein |
| 4,282,884 A | 8/1981 | Boebel |
| 4,306,570 A | 12/1981 | Matthews |
| 4,354,092 A | 10/1982 | Manabe et al. |
| 4,393,879 A | 7/1983 | Milgrom |
| 4,445,509 A | 5/1984 | Auth |
| 4,490,137 A | 12/1984 | Moukheibir |
| 4,549,554 A | 10/1985 | Markham |
| 4,577,629 A | 3/1986 | Martinez |
| 4,589,414 A | 5/1986 | Yoshida et al. |
| 4,603,694 A | 8/1986 | Wheeler |
| 4,605,011 A | 8/1986 | Naslund |
| 4,616,215 A | 10/1986 | Maddalena |
| 4,617,430 A | 10/1986 | Bryant |
| 4,620,539 A | 11/1986 | Andrews et al. |
| 4,643,197 A | 2/1987 | Greene et al. |
| 4,645,153 A | 2/1987 | Granzow et al. |
| 4,678,459 A | 7/1987 | Onik et al. |
| 4,696,298 A | 9/1987 | Higgins et al. |
| 4,702,260 A | 10/1987 | Wang |
| 4,706,687 A | 11/1987 | Rogers |
| 4,776,346 A | 10/1988 | Beraha et al. |
| 4,792,327 A | 12/1988 | Swartz |
| 4,832,044 A | 5/1989 | Garg |
| 4,844,064 A | 7/1989 | Thimsen et al. |
| 4,844,087 A | 7/1989 | Garg |
| 4,850,354 A | 7/1989 | McGurk-Burleson et al. |
| 4,893,635 A | 1/1990 | de Groot et al. |
| 4,907,598 A | 3/1990 | Bauer |
| RE33,258 E | 7/1990 | Onik et al. |
| 4,940,061 A | 7/1990 | Terwilliger et al. |
| 4,952,817 A | 8/1990 | Bolan et al. |
| 4,958,625 A | 9/1990 | Bates et al. |
| 4,967,762 A | 11/1990 | DeVries |
| 4,986,278 A | 1/1991 | Ravid et al. |
| 4,986,279 A | 1/1991 | O'Neill |
| 4,986,807 A | 1/1991 | Farr |
| 4,989,614 A | 2/1991 | Dejter, Jr. et al. |
| 5,025,797 A | 6/1991 | Baran |
| 5,048,538 A | 9/1991 | Terwilliger et al. |
| 5,057,822 A | 10/1991 | Hoffman |
| 5,078,603 A | 1/1992 | Cohen |
| 5,125,413 A | 6/1992 | Baran |
| 5,138,245 A | 8/1992 | Mattinger et al. |
| 5,146,921 A | 9/1992 | Terwilliger et al. |
| 5,156,160 A | 10/1992 | Bennett |
| 5,158,528 A | 10/1992 | Walker et al. |
| 5,172,702 A | 12/1992 | Leigh et al. |
| 5,176,628 A | 1/1993 | Charles et al. |
| 5,183,052 A | 2/1993 | Terwilliger |
| 5,197,484 A | 3/1993 | Kornberg et al. |
| 5,211,627 A | 5/1993 | William |
| 5,223,012 A | 6/1993 | Best et al. |
| 5,225,763 A | 7/1993 | Krohn et al. |
| 5,234,000 A | 8/1993 | Hakky et al. |
| 5,236,334 A | 8/1993 | Bennett |
| 5,242,404 A | 9/1993 | Conley et al. |
| 5,249,583 A | 10/1993 | Mallaby |
| 5,254,117 A | 10/1993 | Rigby et al. |
| 5,282,476 A | 2/1994 | Terwilliger |
| 5,282,477 A | 2/1994 | Bauer |
| 5,290,253 A | 3/1994 | Kira |
| 5,305,762 A | 4/1994 | Acorn et al. |
| 5,324,306 A | 6/1994 | Makower et al. |
| 5,334,183 A | 8/1994 | Wuchinich |
| 5,335,671 A | 8/1994 | Clement |
| 5,368,029 A | 11/1994 | Holcombe et al. |
| 5,368,045 A | 11/1994 | Clement et al. |
| 5,383,874 A | 1/1995 | Jackson et al. |
| 5,397,462 A | 3/1995 | Higashijima et al. |
| 5,400,798 A | 3/1995 | Baran |
| 5,439,474 A | 8/1995 | Li |
| 5,458,112 A | 10/1995 | Weaver |
| 5,469,860 A | 11/1995 | De Santis |
| 5,471,994 A | 12/1995 | Guirguis |
| 5,479,486 A | 12/1995 | Saji |
| 5,485,917 A | 1/1996 | Early |
| 5,492,130 A | 2/1996 | Chiou |
| 5,511,556 A | 4/1996 | DeSantis |
| 5,526,822 A | 6/1996 | Burbank et al. |
| 5,535,755 A | 7/1996 | Heske |
| 5,546,957 A | 8/1996 | Heske |
| 5,554,151 A | 9/1996 | Hinchliffe |
| 5,560,373 A | 10/1996 | De Santis |
| 5,564,436 A | 10/1996 | Hakky et al. |
| 5,569,284 A | 10/1996 | Young et al. |
| 5,575,293 A | 11/1996 | Miller et al. |
| 5,591,170 A | 1/1997 | Spievack et al. |
| 5,601,583 A | 2/1997 | Donahue et al. |
| 5,601,585 A | 2/1997 | Banik et al. |
| 5,602,449 A | 2/1997 | Krause et al. |
| 5,612,738 A | 3/1997 | Kim |
| 5,617,874 A | 4/1997 | Baran |
| 5,649,547 A | 7/1997 | Ritchart et al. |
| 5,655,542 A | 8/1997 | Weilandt |
| 5,655,657 A | 8/1997 | Roshdy |
| 5,665,101 A | 9/1997 | Becker et al. |
| 5,669,394 A | 9/1997 | Bergey et al. |
| 5,699,909 A | 12/1997 | Foster |
| 5,700,265 A | 12/1997 | Romano |
| 5,709,697 A | 1/1998 | Ratcliff et al. |
| 5,720,760 A | 2/1998 | Becker et al. |
| 5,735,264 A | 4/1998 | Siczek et al. |
| 5,752,923 A | 5/1998 | Terwilliger |
| 5,755,714 A | 5/1998 | Murphy-Chutorian |
| 5,766,135 A | 6/1998 | Terwilliger |
| 5,769,086 A | 6/1998 | Ritchart et al. |
| 5,769,795 A | 6/1998 | Terwilliger |
| 5,775,333 A | 7/1998 | Burbank et al. |
| 5,779,649 A | 7/1998 | Herbert |
| 5,788,651 A | 8/1998 | Weilandt |
| 5,792,167 A | 8/1998 | Kablik et al. |
| 5,807,282 A | 9/1998 | Fowler |
| 5,817,033 A | 10/1998 | DeSantis et al. |
| 5,817,034 A | 10/1998 | Milliman et al. |
| 5,823,970 A | 10/1998 | Terwilliger |
| 5,827,305 A | 10/1998 | Gordon |
| 5,830,219 A | 11/1998 | Bird et al. |
| D403,405 S | 12/1998 | Terwilliger |
| 5,857,982 A | 1/1999 | Milliman et al. |
| 5,871,699 A | 2/1999 | Ruggeri |

(56) References Cited

U.S. PATENT DOCUMENTS

| | | |
|---|---|---|
| 5,879,365 A | 3/1999 | Whitfield et al. |
| 5,908,233 A | 6/1999 | Heskett et al. |
| 5,913,857 A | 6/1999 | Ritchart et al. |
| 5,916,198 A | 6/1999 | Dillow |
| 5,916,229 A | 6/1999 | Evans |
| 5,928,164 A | 7/1999 | Burbank et al. |
| 5,944,673 A | 8/1999 | Gregoire et al. |
| 5,951,490 A | 9/1999 | Fowler |
| 5,951,575 A | 9/1999 | Bolduc et al. |
| 5,964,716 A | 10/1999 | Gregoire et al. |
| 5,971,939 A | 10/1999 | DeSantis et al. |
| 5,976,164 A | 11/1999 | Bencini et al. |
| 5,980,469 A | 11/1999 | Burbank et al. |
| 5,980,545 A | 11/1999 | Pacala et al. |
| 6,007,495 A | 12/1999 | Matula |
| 6,007,497 A | 12/1999 | Huitema |
| 6,007,556 A | 12/1999 | Kablik et al. |
| 6,017,316 A | 1/2000 | Ritchart et al. |
| 6,018,227 A | 1/2000 | Kumar et al. |
| 6,019,733 A | 2/2000 | Farascioni |
| 6,022,324 A | 2/2000 | Skinner |
| 6,022,325 A | 2/2000 | Siczek et al. |
| 6,027,458 A | 2/2000 | Janssens |
| 6,032,673 A | 3/2000 | Savage et al. |
| 6,036,657 A | 3/2000 | Milliman et al. |
| 6,050,955 A | 4/2000 | Bryan et al. |
| 6,055,870 A | 5/2000 | Jaeger |
| 6,071,247 A | 6/2000 | Kennedy |
| 6,077,230 A | 6/2000 | Gregoire et al. |
| 6,083,176 A | 7/2000 | Terwilliger |
| 6,083,237 A | 7/2000 | Huitema et al. |
| 6,086,544 A | 7/2000 | Hibner et al. |
| 6,106,484 A | 8/2000 | Terwilliger |
| 6,110,129 A | 8/2000 | Terwilliger |
| 6,120,462 A | 9/2000 | Hibner et al. |
| 6,123,957 A | 9/2000 | Jernberg |
| 6,126,617 A | 10/2000 | Weilandt et al. |
| 6,142,955 A | 11/2000 | Farascioni et al. |
| 6,162,187 A | 12/2000 | Buzzard et al. |
| 6,165,136 A | 12/2000 | Nishtala |
| 6,193,673 B1 | 2/2001 | Viola et al. |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,231,522 B1 | 5/2001 | Voegele et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,434,507 B1 | 8/2002 | Clayton et al. |
| 6,436,054 B1 | 8/2002 | Viola et al. |
| 6,461,302 B1 | 10/2002 | Thompson |
| 6,471,659 B2 | 10/2002 | Eggers et al. |
| 6,482,158 B2 | 11/2002 | Mault |
| 6,485,436 B1 | 11/2002 | Truckai et al. |
| 6,488,636 B2 | 12/2002 | Bryan et al. |
| 6,494,844 B1 | 12/2002 | Van Bladel et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,544,194 B1 | 4/2003 | Kortenbach et al. |
| 6,551,255 B2 | 4/2003 | Van Bladel et al. |
| 6,554,779 B2 | 4/2003 | Viola et al. |
| 6,585,664 B2 | 7/2003 | Burdorff et al. |
| 6,585,694 B1 | 7/2003 | Smith et al. |
| 6,586,585 B1 | 7/2003 | Bastian |
| 6,592,530 B1 | 7/2003 | Farhadi |
| 6,626,849 B2 | 9/2003 | Huitema et al. |
| 6,632,182 B1 | 10/2003 | Treat |
| 6,638,235 B2 | 10/2003 | Miller et al. |
| 6,656,133 B2 | 12/2003 | Voegele et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,702,832 B2 | 3/2004 | Ross et al. |
| 6,712,773 B1 | 3/2004 | Viola |
| 6,712,774 B2 | 3/2004 | Voegele et al. |
| 6,752,768 B2 | 6/2004 | Burdorff et al. |
| 6,753,671 B1 | 6/2004 | Harvey |
| 6,755,802 B2 | 6/2004 | Bell |
| 6,758,824 B1 | 7/2004 | Miller et al. |
| 6,764,495 B2 | 7/2004 | Lee et al. |
| 6,832,990 B2 | 12/2004 | Kortenbach et al. |
| 6,849,080 B2 | 2/2005 | Lee et al. |
| 6,850,159 B1 | 2/2005 | Mudge |
| 6,860,860 B2 | 3/2005 | Viola |
| 6,875,183 B2 | 4/2005 | Cervi |
| 6,887,210 B2 | 5/2005 | Quay |
| 6,908,440 B2 | 6/2005 | Fisher |
| D508,458 S | 8/2005 | Solland et al. |
| 6,926,676 B2 | 8/2005 | Turturro et al. |
| 6,984,213 B2 | 1/2006 | Horner et al. |
| 7,004,174 B2 | 2/2006 | Eggers et al. |
| 7,010,332 B1 | 3/2006 | Irvin et al. |
| 7,025,732 B2 | 4/2006 | Thompson et al. |
| D525,583 S | 7/2006 | Vu |
| 7,108,660 B2 | 9/2006 | Stephens et al. |
| 7,153,274 B2 | 12/2006 | Stephens et al. |
| 7,156,814 B1 | 1/2007 | Williamson, IV et al. |
| 7,182,754 B2 | 2/2007 | Brigham et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,252,641 B2 | 8/2007 | Thompson et al. |
| 7,276,032 B2 | 10/2007 | Hibner |
| 7,328,794 B2 | 2/2008 | Lubs et al. |
| 7,347,828 B2 | 3/2008 | Francese et al. |
| 7,347,829 B2 | 3/2008 | Mark et al. |
| 7,374,544 B2 | 5/2008 | Freeman et al. |
| 7,390,306 B2 | 6/2008 | Mark |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,419,472 B2 | 9/2008 | Hibner et al. |
| 7,432,813 B2 | 10/2008 | Postma |
| 7,452,367 B2 | 11/2008 | Rassman et al. |
| 7,458,940 B2 | 12/2008 | Miller |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,491,177 B2 | 2/2009 | Hibner |
| 7,494,473 B2 | 2/2009 | Eggers et al. |
| 7,497,833 B2 | 3/2009 | Miller |
| 7,510,534 B2 | 3/2009 | Burdorff et al. |
| 7,513,877 B2 | 4/2009 | Viola |
| 7,517,321 B2 | 4/2009 | McCullough et al. |
| 7,517,322 B2 | 4/2009 | Weikel, Jr. et al. |
| 7,549,978 B2 | 6/2009 | Carlson et al. |
| 7,575,557 B2 | 8/2009 | Morton et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,758,515 B2 | 7/2010 | Hibner |

(56) References Cited

U.S. PATENT DOCUMENTS

| | | |
|---|---|---|
| 7,762,961 B2 | 7/2010 | Heske et al. |
| 7,806,834 B2 | 10/2010 | Beckman et al. |
| 7,828,746 B2 | 11/2010 | Teague |
| 7,828,747 B2 | 11/2010 | Heske et al. |
| 7,841,991 B2 | 11/2010 | Douglas et al. |
| 7,854,706 B2 | 12/2010 | Hibner |
| 7,862,517 B2 | 1/2011 | Tsonton et al. |
| 7,871,384 B2 | 1/2011 | Thompson et al. |
| 7,883,476 B2 | 2/2011 | Miller et al. |
| 7,883,494 B2 | 2/2011 | Martin |
| 7,906,076 B2 | 3/2011 | Fischer |
| 7,914,462 B2 | 3/2011 | Hutchins et al. |
| 7,959,580 B2 | 6/2011 | Mccullough et al. |
| 7,974,681 B2 | 7/2011 | Wallace et al. |
| 8,002,713 B2 | 8/2011 | Heske et al. |
| 8,012,102 B2 | 9/2011 | McCullough et al. |
| 8,016,772 B2 | 9/2011 | Heske et al. |
| 8,016,844 B2 | 9/2011 | Privitera et al. |
| 8,052,614 B2 | 11/2011 | Heske et al. |
| 8,052,615 B2 | 11/2011 | Reuber et al. |
| 8,073,008 B2 | 12/2011 | Mehta et al. |
| 8,083,671 B2 | 12/2011 | Boulais et al. |
| 8,109,885 B2 | 2/2012 | Heske et al. |
| 8,118,755 B2 | 2/2012 | Hibner et al. |
| 8,152,738 B2 | 4/2012 | Li et al. |
| 8,157,744 B2 | 4/2012 | Jorgensen et al. |
| 8,162,851 B2 | 4/2012 | Heske et al. |
| 8,172,773 B2 | 5/2012 | Heske et al. |
| 8,187,204 B2 | 5/2012 | Miller et al. |
| 8,190,238 B2 | 5/2012 | Moll et al. |
| 8,206,409 B2 | 6/2012 | Privitera et al. |
| 8,251,916 B2 | 8/2012 | Speeg et al. |
| 8,251,917 B2 | 8/2012 | Almazan |
| 8,262,585 B2 | 9/2012 | Thompson et al. |
| 8,262,586 B2 | 9/2012 | Anderson et al. |
| 8,267,868 B2 | 9/2012 | Taylor et al. |
| 8,277,393 B2 | 10/2012 | Miller et al. |
| 8,282,574 B2 | 10/2012 | Coonahan et al. |
| 8,313,444 B2 | 11/2012 | Thompson et al. |
| 8,343,069 B2 | 1/2013 | Uchiyama et al. |
| 8,366,636 B2 | 2/2013 | Videbaek |
| 8,430,824 B2 | 4/2013 | Videbaek et al. |
| 8,430,827 B2 | 4/2013 | Nicoson et al. |
| 8,485,989 B2 | 7/2013 | Videbaek |
| 8,597,206 B2 | 12/2013 | Videback |
| 8,702,621 B2 | 4/2014 | Mccullough et al. |
| 8,702,622 B2 | 4/2014 | McCullough et al. |
| 8,771,200 B2 | 7/2014 | Thompson et al. |
| 8,864,680 B2 | 10/2014 | Videbæk et al. |
| 8,926,527 B2 | 1/2015 | Jørgensen et al. |
| 8,956,306 B2 | 2/2015 | Hibner |
| 8,961,430 B2 | 2/2015 | Coonahan et al. |
| 8,992,440 B2 | 3/2015 | Reuber et al. |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0000403 A1 | 1/2002 | Tanaka et al. |
| 2002/0029007 A1 | 3/2002 | Bryan et al. |
| 2002/0065474 A1 | 5/2002 | Viola |
| 2002/0067151 A1 | 6/2002 | Tanishita |
| 2002/0068878 A1 | 6/2002 | Jasonni et al. |
| 2002/0082518 A1 | 6/2002 | Weiss et al. |
| 2002/0107043 A1 | 8/2002 | Adamson et al. |
| 2002/0115942 A1 | 8/2002 | Stanford et al. |
| 2002/0120212 A1 | 8/2002 | Ritchart et al. |
| 2002/0143269 A1 | 10/2002 | Neuenfeldt |
| 2002/0156395 A1 | 10/2002 | Stephens et al. |
| 2003/0023188 A1 | 1/2003 | Kritzman et al. |
| 2003/0023239 A1 | 1/2003 | Burbank et al. |
| 2003/0073929 A1 | 4/2003 | Baltschun et al. |
| 2003/0093103 A1 | 5/2003 | Malackowski et al. |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0034280 A1 | 2/2004 | Privitera et al. |
| 2004/0049128 A1 | 3/2004 | Miller et al. |
| 2004/0054299 A1 | 3/2004 | Burdorff et al. |
| 2004/0082915 A1 | 4/2004 | Kadan |
| 2004/0092980 A1 | 5/2004 | Cesarini et al. |
| 2004/0092992 A1 | 5/2004 | Adams et al. |
| 2004/0162505 A1 | 8/2004 | Kaplan et al. |
| 2004/0167428 A1 | 8/2004 | Quick et al. |
| 2004/0186393 A1 | 9/2004 | Leigh et al. |
| 2004/0210161 A1 | 10/2004 | Burdorff et al. |
| 2004/0215103 A1 | 10/2004 | Mueller, Jr. et al. |
| 2004/0220495 A1 | 11/2004 | Cahir et al. |
| 2004/0230135 A1 | 11/2004 | Merkle |
| 2004/0230188 A1 | 11/2004 | Cioanta et al. |
| 2004/0249278 A1 | 12/2004 | Krause |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0054947 A1 | 3/2005 | Goldenberg |
| 2005/0065453 A1 | 3/2005 | Shabaz et al. |
| 2005/0080355 A1 | 4/2005 | Mark |
| 2005/0085838 A1 | 4/2005 | Thompson et al. |
| 2005/0088120 A1 | 4/2005 | Avis |
| 2005/0101879 A1 | 5/2005 | Shidham et al. |
| 2005/0113715 A1 | 5/2005 | Schwindt et al. |
| 2005/0113716 A1 | 5/2005 | Mueller, Jr. et al. |
| 2005/0124914 A1 | 6/2005 | Dicarlo et al. |
| 2005/0124915 A1 | 6/2005 | Eggers et al. |
| 2005/0165328 A1 | 7/2005 | Heske et al. |
| 2005/0177117 A1 | 8/2005 | Crocker et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0215921 A1 | 9/2005 | Hibner et al. |
| 2005/0275378 A1 | 12/2005 | Canino et al. |
| 2005/0277829 A1 | 12/2005 | Tsonton et al. |
| 2005/0277871 A1 | 12/2005 | Selis |
| 2005/0288605 A1 | 12/2005 | Pellegrino et al. |
| 2006/0030784 A1 | 2/2006 | Miller et al. |
| 2006/0074344 A1 | 4/2006 | Hibner |
| 2006/0074345 A1 | 4/2006 | Hibner |
| 2006/0074350 A1 | 4/2006 | Cash |
| 2006/0113958 A1 | 6/2006 | Lobert et al. |
| 2006/0116603 A1 | 6/2006 | Shibazaki et al. |
| 2006/0122535 A1 | 6/2006 | Daum |
| 2006/0129063 A1 | 6/2006 | Thompson et al. |
| 2006/0149162 A1 | 7/2006 | Daw et al. |
| 2006/0173377 A1 | 8/2006 | McCullough et al. |
| 2006/0178666 A1 | 8/2006 | Cosman et al. |
| 2006/0184063 A1 | 8/2006 | Miller |
| 2006/0200042 A1 | 9/2006 | Weikel, Jr. et al. |
| 2006/0241515 A1 | 10/2006 | Jones et al. |
| 2006/0258956 A1 | 11/2006 | Haberstich et al. |
| 2006/0260994 A1 | 11/2006 | Mark et al. |
| 2007/0016101 A1 | 1/2007 | Feldman et al. |
| 2007/0027407 A1 | 2/2007 | Miller |
| 2007/0032741 A1 | 2/2007 | Hibner et al. |
| 2007/0032743 A1 | 2/2007 | Hibner |
| 2007/0055173 A1 | 3/2007 | DeLonzor et al. |
| 2007/0073326 A1 | 3/2007 | Miller et al. |
| 2007/0090788 A1 | 4/2007 | Hansford et al. |
| 2007/0106176 A1 | 5/2007 | Mark et al. |
| 2007/0118048 A1 | 5/2007 | Stephens et al. |
| 2007/0118049 A1 | 5/2007 | Viola |
| 2007/0123797 A1 | 5/2007 | Krause |
| 2007/0149893 A1 | 6/2007 | Heske et al. |

(56) References Cited

U.S. PATENT DOCUMENTS

| | | |
|---|---|---|
| 2007/0149894 A1 | 6/2007 | Heske et al. |
| 2007/0161925 A1 | 7/2007 | Quick et al. |
| 2007/0167736 A1 | 7/2007 | Dietz et al. |
| 2007/0167782 A1 | 7/2007 | Callahan et al. |
| 2007/0167828 A1 | 7/2007 | Saadat |
| 2007/0167943 A1 | 7/2007 | Janssen et al. |
| 2007/0179401 A1 | 8/2007 | Hibner |
| 2007/0213590 A1 | 9/2007 | Squicciarini |
| 2007/0213630 A1 | 9/2007 | Beckman et al. |
| 2007/0213632 A1 | 9/2007 | Okazaki et al. |
| 2007/0219572 A1 | 9/2007 | Deck et al. |
| 2007/0236180 A1 | 10/2007 | Rodgers |
| 2007/0239067 A1 | 10/2007 | Hibner et al. |
| 2007/0255173 A1 | 11/2007 | Hibner |
| 2007/0270710 A1 | 11/2007 | Frass et al. |
| 2007/0276288 A1 | 11/2007 | Khaw |
| 2007/0287933 A1 | 12/2007 | Phan et al. |
| 2007/0292858 A1 | 12/2007 | Chen et al. |
| 2007/0293788 A1 | 12/2007 | Entrekin et al. |
| 2007/0293830 A1 | 12/2007 | Martin |
| 2008/0004545 A1 | 1/2008 | Garrison |
| 2008/0007217 A1 | 1/2008 | Riley |
| 2008/0015429 A1 | 1/2008 | Tsonton et al. |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0071193 A1 | 3/2008 | Reuber et al. |
| 2008/0079391 A1 | 4/2008 | Schroeck et al. |
| 2008/0103411 A1 | 5/2008 | Van Bladel et al. |
| 2008/0110261 A1 | 5/2008 | Randall et al. |
| 2008/0125634 A1 | 5/2008 | Ryan et al. |
| 2008/0135443 A1 | 6/2008 | Frojd et al. |
| 2008/0146962 A1 | 6/2008 | Ritchie et al. |
| 2008/0146965 A1 | 6/2008 | Privitera et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson et al. |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bickenbach |
| 2008/0214955 A1 | 9/2008 | Speeg et al. |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0287826 A1 | 11/2008 | Videbaek et al. |
| 2008/0306406 A1 | 12/2008 | Thompson et al. |
| 2008/0308607 A1 | 12/2008 | Timm et al. |
| 2008/0319341 A1 | 12/2008 | Taylor et al. |
| 2009/0015208 A1 | 1/2009 | White et al. |
| 2009/0030405 A1 | 1/2009 | Quick et al. |
| 2009/0146609 A1 | 1/2009 | Santos |
| 2009/0048532 A1 | 2/2009 | Stephens et al. |
| 2009/0048533 A1 | 2/2009 | Miller |
| 2009/0062624 A1 | 3/2009 | Neville |
| 2009/0082695 A1 | 3/2009 | Whitehead |
| 2009/0087249 A1 | 4/2009 | Flagle et al. |
| 2009/0088666 A1 | 4/2009 | Miller et al. |
| 2009/0112118 A1 | 4/2009 | Quick, Jr. et al. |
| 2009/0125062 A1 | 5/2009 | Amin |
| 2009/0137927 A1 | 5/2009 | Miller |
| 2009/0171243 A1 | 7/2009 | Hibner et al. |
| 2009/0204022 A1 | 8/2009 | Schwindt |
| 2009/0227893 A1 | 9/2009 | Coonahan et al. |
| 2009/0281453 A1 | 11/2009 | Tsonton et al. |
| 2010/0030020 A1 | 2/2010 | Sanders et al. |
| 2010/0063416 A1 | 3/2010 | Cicenas et al. |
| 2010/0106053 A1 | 4/2010 | Videbaek et al. |
| 2010/0152610 A1 | 6/2010 | Parihar et al. |
| 2010/0152611 A1 | 6/2010 | Parihar et al. |
| 2010/0160820 A1 | 6/2010 | Weikel, Jr. et al. |
| 2010/0210966 A1 | 8/2010 | Videbaek |
| 2010/0222700 A1 | 9/2010 | Hibner |
| 2010/0292607 A1 | 11/2010 | Moore et al. |
| 2010/0312140 A1 | 12/2010 | Smith et al. |
| 2010/0317995 A1 | 12/2010 | Hibner et al. |
| 2010/0317997 A1 | 12/2010 | Hibner et al. |
| 2010/0317998 A1 | 12/2010 | Hibner et al. |
| 2011/0021946 A1 | 1/2011 | Heske et al. |
| 2011/0054350 A1 | 3/2011 | Videbaek |
| 2011/0077551 A1 | 3/2011 | Videbaek |
| 2011/0087131 A1 | 4/2011 | Videbaek |
| 2011/0105945 A1 | 5/2011 | Videbaek et al. |
| 2011/0105946 A1 | 5/2011 | Sorensen et al. |
| 2011/0152715 A1 | 6/2011 | Delap et al. |
| 2011/0160611 A1 | 6/2011 | Ritchart et al. |
| 2011/0208085 A1 | 8/2011 | Mccullough et al. |
| 2011/0295150 A1 | 12/2011 | Mccullough et al. |
| 2012/0071787 A1 | 3/2012 | Reuber et al. |
| 2012/0095366 A1 | 4/2012 | Heske et al. |
| 2012/0184873 A1 | 7/2012 | Jorgensen et al. |
| 2012/0191009 A1 | 7/2012 | Hoon et al. |
| 2012/0203135 A1 | 8/2012 | Heske et al. |
| 2012/0215130 A1 | 8/2012 | Field et al. |
| 2012/0238905 A1 | 9/2012 | Heske et al. |
| 2012/0310109 A1 | 12/2012 | Almazan |
| 2012/0323120 A1 | 12/2012 | Taylor et al. |
| 2012/0323140 A1 | 12/2012 | Taylor et al. |
| 2012/0330185 A1 | 12/2012 | Coonahan et al. |
| 2013/0023789 A1 | 1/2013 | Anderson et al. |
| 2013/0023791 A1 | 1/2013 | Thompson et al. |
| 2013/0289441 A1 | 10/2013 | Videbaek et al. |
| 2014/0228706 A1 | 8/2014 | Mccullough et al. |
| 2014/0371585 A1 | 12/2014 | Thompson et al. |
| 2015/0025415 A1 | 1/2015 | Videbaek et al. |
| 2015/0094613 A1 | 4/2015 | Jorgensen et al. |
| 2015/0133814 A1 | 5/2015 | Almazan |
| 2015/0148702 A1 | 5/2015 | Heske et al. |
| 2015/0190124 A1 | 7/2015 | McCullough et al. |
| 2015/0238174 A1 | 8/2015 | Reuber et al. |
| 2015/0342579 A1 | 12/2015 | Heske et al. |
| 2016/0256138 A1 | 9/2016 | Videbaek et al. |
| 2016/0367229 A1 | 12/2016 | Jorgensen et al. |
| 2016/0367230 A1 | 12/2016 | Suzuki et al. |
| 2016/0374650 A1 | 12/2016 | Heske et al. |
| 2017/0042517 A1 | 2/2017 | Heske et al. |

FOREIGN PATENT DOCUMENTS

| | | |
|---|---|---|
| DE | 3924291 A1 | 1/1991 |
| DE | 4041614 C1 | 10/1992 |
| DE | 10034297 A1 | 4/2001 |
| DE | 10026303 A1 | 2/2002 |
| DE | 20204363 U1 | 5/2002 |
| DE | 20209525 U1 | 11/2002 |
| DE | 10235480 A1 | 2/2004 |
| EP | 0433717 A1 | 6/1991 |
| EP | 0890339 A1 | 1/1999 |
| EP | 0995400 A1 | 4/2000 |
| EP | 1074271 A2 | 2/2001 |
| EP | 1520518 A2 | 4/2005 |
| EP | 1579809 A1 | 9/2005 |
| EP | 1604615 A1 | 12/2005 |
| EP | 1665989 A2 | 6/2006 |
| EP | 1698282 A1 | 9/2006 |
| EP | 1829487 A1 | 9/2007 |
| EP | 2095772 A1 | 9/2009 |
| EP | 2106750 A2 | 10/2009 |
| EP | 1569561 B1 | 10/2010 |
| FR | 1345429 A | 12/1963 |
| FR | 2739293 A1 | 4/1997 |
| GB | 2018601 A | 10/1979 |

(56) References Cited

FOREIGN PATENT DOCUMENTS

| | | | |
|---|---|---|---|
| GB | 2323288 | A | 9/1998 |
| JP | 1-126957 | A | 9/1987 |
| JP | H10508504 | A | 8/1998 |
| JP | 2005530554 | A | 10/2005 |
| JP | 2006509545 | A | 3/2006 |
| JP | 2006528907 | A | 12/2006 |
| JP | 2007502159 | A | 2/2007 |
| WO | 9508945 | A2 | 4/1995 |
| WO | 9624289 | A2 | 8/1996 |
| WO | 9628097 | A1 | 9/1996 |
| WO | 9734531 | A1 | 9/1997 |
| WO | 9825522 | A1 | 6/1998 |
| WO | 9831285 | A1 | 7/1998 |
| WO | 9835615 | A1 | 8/1998 |
| WO | 9846290 | A1 | 10/1998 |
| WO | 9933501 | A1 | 7/1999 |
| WO | 0004832 | A1 | 2/2000 |
| WO | 0030546 | A1 | 6/2000 |
| WO | 0059378 | A2 | 10/2000 |
| WO | 0172230 | A1 | 10/2001 |
| WO | 0222023 | A1 | 3/2002 |
| WO | 0232318 | A1 | 4/2002 |
| WO | 02069808 | A2 | 9/2002 |
| WO | 2005013830 | A1 | 2/2005 |
| WO | 2006005342 | A1 | 1/2006 |
| WO | 2006015302 | A1 | 2/2006 |
| WO | 2007047128 | A1 | 4/2007 |
| WO | 2007095330 | A2 | 8/2007 |
| WO | 2007112751 | A2 | 10/2007 |
| WO | 2008021687 | A1 | 2/2008 |
| WO | 2008024684 | A2 | 2/2008 |
| WO | 2008040812 | A1 | 4/2008 |
| WO | 2008131362 | A2 | 10/2008 |
| WO | 2011019343 | A1 | 2/2011 |

TISSUE HANDLING SYSTEM WITH REDUCED OPERATOR EXPOSURE

PRIORITY DATA AND INCORPORATION BY REFERENCE

This application is a continuation of U.S. patent application Ser. No. 14/514,660, filed Oct. 15, 2014, now U.S. Pat. No. 9,566,045, which is a continuation of U.S. patent application Ser. No. 13/931,116, filed Jun. 28, 2013, now abandoned, which is a continuation of U.S. patent application Ser. No. 12/444,084, filed Nov. 25, 2009, now U.S. Pat. No. 8,485,987, which is a U.S. national phase of International Application No. PCT/EP2007/060615, filed Oct. 5, 2007, which claims priority to U.S. Provisional Application Ser. No. 60/850,004, filed Oct. 6, 2006, each of which is hereby incorporated by reference in its entirety.

FIELD OF THE INVENTION

This invention relates to systems for the acquisition and handling of tissue samples and, more particularly, to a system that comprises all necessary means for harvesting, storing and transporting tissue samples without requiring physical handling of the tissue sample by the operator, in an uninterrupted chain that has its point of origin within the body of the patient and has as its point of conclusion the commencement of analysis of the at least one sample by a pathologist or similarly medical skilled professional. More specifically, the invention relates to a system for the acquisition and handling of tissue samples that comprises all necessary means for harvesting, storing and transporting the at least one tissue sample without requiring physical handling of the sample by the operator, in an uninterrupted tissue handling chain that has its point of origin within the body of the patient and has as its point of conclusion the commencement of analysis of the at least one tissue sample by a pathologist or similarly skilled professional, while at the same time protecting the operator and other persons involved in the handling of tissue samples from exposure to potential bio-hazards and bio-contaminants as well as formalin or similar preserving agents that may act as carcinogens.

BACKGROUND OF THE INVENTION

In modern medicine it is often desirable and frequently necessary to harvest tissue samples from a target tissue region or tissue site inside a human or animal body for the purpose of diagnosing a suspected malignancy. Currently available biopsy devices offer several ways of accessing suspect tissue and of harvesting tissue samples that may be used for diagnostic purposes, and some also comprise temporary storage solutions that may be used to hold tissue samples during a biopsy procedure. Such a biopsy device is disclosed in U.S. Pat. No. 5,526,822. The disclosed biopsy device is capable of harvesting multiple tissue samples in a single device insertion and features a cassette with multiple tissue chambers, permitting the temporary storage of multiple tissue samples.

However, none of the currently available biopsy devices and systems address all the functions and provide all the interfaces between functions that are involved in harvesting a tissue sample and getting the tissue sample to the pathologist in uncontaminated or undisturbed condition. Another important aspect of the present invention is to provide biopsy devices and systems that minimize operator exposure to bio-hazards, bio-contaminants as well as formalin and other known and probable human carcinogens. The current lack of commercially available biopsy devices and systems with one or both of these capabilities is problematic for several reasons.

New and improved diagnostic techniques—such as cytogenetic, immunological and biochemical analyses require that the tissue samples be handled with extreme care. Since tissue architecture is an important parameter in the histologic analysis of samples it is important that handling of acquired tissue samples is minimized.

Human tissues are potentially infectious, and an operator increases his exposure to such infection by physically handling tissue samples. Given this, limiting operator exposure to tissue samples is a sensible precaution. Currently available systems, such as is disclosed in U.S. Pat. No. 5,526,822, provide means for temporarily storing one or more tissue samples during a biopsy procedure, but no means are provided for transferring such tissue samples to more permanent storage containers where preservation and fixation of the tissue samples is possible. In use, these systems therefore require that the operator or an assistant manually transfer samples from the temporary storage means included in the biopsy device to more permanent storage means if said samples are to be fixated prior to being sent to a pathologist or similarly skilled individual for analysis.

Another problem that has received little attention in the design of presently available biopsy systems is the use of formalin or similar preserving agents to fixate tissue samples subsequent to their extraction from the patient. Formalin is classified by the WHO and IARC as a known carcinogen and at least some countries have imposed limits on the permissible exposure. These limits include upper limits on the amount of airborne formalin and such upper limits have forced some hospitals to implement ventilation and suction systems to protect doctors and assistants from excessive exposure to formalin. Such implementation programs—when possible—are costly and potentially disruptive to established biopsy procedure routines.

Therefore, a biopsy device and system according to the present invention that comprise all necessary components and functionalities for safely and efficiently harvesting one or more tissue samples in a single device insertion are highly advantageous. Furthermore, such biopsy device and system may advantageously comprise means for temporarily storing harvested tissue samples in individual compartments during the biopsy procedure while permitting the operator/doctor to inspect each tissue sample for adequacy, as well as means for more permanently storing and fixating the samples once the harvesting is over. Ideally, transfer of the tissue samples between the temporary storage means included in the biopsy device and the permanent storage means should be possible without requiring that the operator removes the samples from their individual compartments thereby minimizing the exposure of the operator to bio-hazards and bio-contamination. In addition, such a comprehensive biopsy device and system would also provide means for aggregating formalin or a similar preserving and fixating agent while maintaining at all times a closed environment, to eliminate operator exposure to such substances.

SUMMARY OF THE INVENTION

In a first aspect, the present invention provides a tissue handling system comprising:
  a biopsy device having an invasive unit with tissue-receiving and tissue-severing components being capable of harvesting and bringing at least one tissue sample to a point outside the body of a patient;

a tissue collecting device adapted to be brought in detachable operative engagement with the tissue-receiving components of the biopsy device to remove the at least one tissue sample;

a tissue storage container configured to receive the at least one tissue sample, the entire tissue collecting device, or the part of the collecting device that contains the at least one tissue sample, the tissue storage container further being configured to receive a volume of preserving agent; and a vessel adapted to contain the preserving agent adapted to be gas-tightly mated or coupled to the tissue storage container.

Preferably, structure is provided for transferring (i.e. conveying or moving) the preserving agent in the vessel to the tissue storage container. As the tissue collecting device may be detached from the remaining components of the biopsy device and placed in the tissue storage container, which in turn may be partially or fully filled with the preserving agent deriving from the vessel, a convenient way of transferring tissue samples from the biopsy device to a storage container is provided.

A compartment in the vessel for storing the preserving agent may be closed by a liquid and gas tight closure, which is releasable when the vessel is mated or coupled to the tissue storage container. In one embodiment, preserving agent may be released following a predefined user action, such as removal of a separate seal or closure or activation of a syringe plunger. In other embodiments, release of the closure to convey preserving agent from the vessel may occur automatically as a consequence of attachment of the vessel to the tissue storage container. For example, the tissue storage container and the vessel may comprise a connecting structure for gas-tightly mating or coupling the vessel to the tissue storage container. Hence, the connecting structure may be arranged to cause the closure to be released as a consequence of mating or coupling the vessel to the tissue storage container.

The vessel may be comprised in a lid for closing the tissue storage container. In one embodiment, the lid is attachable to the tissue storage container in such a way that a first attachment action establishes a gas tight coupling of the vessel to the tissue storage container, and a second attachment action causes release of the closure. The tissue storage container and the lid are preferably arranged such that the second attachment action cannot occur prior to the first attachment action. The first attachment action may e.g. include an axial displacement of the parts relative to each other, whereas the second attachment action may e.g. include a mutual twisting of the parts. The parts may be shaped and configured such that the twisting, which causes release of the closure cannot occur, before the parts are arranged in the correct axial inter-relationship. Preferably, the closure may be resealed following a third pre-defined user action, such as e.g. a further mutual twisting of the parts, to prevent the preserving agent from flowing back from the tissue storage container into the vessel.

In other embodiments, the vessel may include a syringe, and the tissue storage container may comprise a connecting mechanism for gas-tightly mating or coupling the syringe to the tissue storage container, such as a luer lock or a septum.

The collecting device of the biopsy device may comprise a collecting unit which comprises a plurality of individual tissue chambers, and wherein the collecting device is capable of sequentially removing, from the tissue-receiving components of the biopsy device, a plurality of individual tissue samples as they are excised from the body of the patient and of temporarily storing the tissue samples in individual tissue chambers. Alternatively, the tissue samples may be temporarily stored in one single bulk in said chamber.

Suitable devices for harvesting and temporarily storing tissue samples are disclosed in International Patent Application No. PCT/DK2007/000166, which is hereby incorporated by reference.

The volume of preserving agent in the vessel is preferably sufficient to cover the at least one tissue sample when stored in the tissue storage container.

In a second aspect, the present invention provides a method of handling at least one harvested biopsy tissue sample, the method comprising:

providing the at least one tissue sample in tissue-receiving components of a biopsy device outside the body of a patient;

detachably engaging a tissue collecting device to said tissue-receiving components;

arranging the at least one tissue sample, the entire tissue collecting device, or the part of the collecting device that contains the at least one tissue sample in a tissue storage container;

gas-tightly mating or coupling a vessel containing a volume of a preserving agent to the tissue storage container;

transferring the volume of preserving agent from the vessel to the tissue storage container, when the vessel is gas-tightly mated or coupled to the tissue storage container.

The features of the system of the first aspect of the invention and their intended method of use may be incorporated in embodiments of the method of the second aspect of the invention.

It will hence be understood that the vessel may include a compartment for storing the preserving agent, wherein the compartment is closed by a liquid and gas tight closure, and wherein the closure is released from a closed condition to an open condition, when the vessel is mated or coupled to the tissue storage container. The closure may be caused to be released as a consequence of mating or coupling the vessel to the tissue storage container. The vessel may be comprised in a lid for closing the tissue storage container, and the lid may be attached to the tissue storage container in such a way that a first attachment action establishes a gas tight coupling of the vessel to the tissue storage container, and a second subsequent attachment action causes release of said closure. A third subsequent action may cause closing of the closure to prevent preserving agent from flowing back from the tissue storage container to the vessel.

The method may further comprise, subsequently to the step of transferring, the further step of conveying the tissue storage container with the at least one tissue sample container therein from a first handling site to a second handling site, when the tissue sample container is closed by said lid. The first handling site may e.g. be provided close to the patient, e.g. on a working desk of the surgeon performing the biopsy procedure, and the second handling site may e.g. be provided at a remote location, such as the analysis site of the pathologist.

In a third aspect, the invention provides a system for storing at least one harvested biopsy tissue sample, the system comprising:

a tissue storage container capable of receiving and storing the at least one tissue sample;

a vessel containing a volume of a preserving agent;
a connecting structure for gas-tightly mating or coupling the vessel to the tissue storage container;
a fluid transferring mechanism for causing a transfer of the volume of preserving agent from the vessel to the tissue storage container, when the vessel is gas-tightly mated or coupled to the tissue storage container.

The features of the system of the first aspect of the invention and the method of the second aspect of the invention also apply to the system of the third aspect of the invention. It will hence be appreciated that the vessel may have a compartment for storing the preserving agent, wherein the compartment is closed by a liquid and gas tight closure, the closure being releasable when the vessel is mated or coupled to the tissue storage container. The tissue storage container and the vessel may comprise a connecting structure for gas-tightly mating or coupling the vessel to the tissue storage container, and the connecting structure may be arranged to cause the closure to be released as a consequence of mating or coupling the vessel to the tissue storage container. The vessel may be comprised in a lid for closing the tissue storage container. The lid may be attachable to the tissue storage container in such a way that a first attachment action establishes a gas tight coupling of the vessel to the tissue storage container, and a second attachment action causes release of said closure, the tissue storage container and the lid being arranged such that the second attachment action cannot occur prior to the first attachment action. A third subsequent action may cause closing of the closure to prevent preserving agent from flowing back from the tissue storage container to the vessel.

The vessel may include a syringe, and the tissue storage container may comprise a connecting mechanism for gas-tightly mating or coupling the syringe to the tissue storage container.

The vessel may be adapted to contain a volume of preserving agent, which is sufficient to cover the at least one tissue sample when stored in the tissue storage container.

It will be appreciated that the system of the third aspect of the invention may be used to cause the transfer of any matter into any kind of container. Hence, the system of the third aspect of the invention may be for storing any kind of material with any kind of liquid or gas, or for mixing two components, such as two kinds of liquid, two kinds of powders, or for mixing liquid into solid matter or powder.

In a fourth aspect, the present invention provides a vessel for a system according to the third aspect of the invention, said system comprising a tissue storage container capable of receiving and storing at least one tissue sample, the vessel comprising:
a cavity containing a volume of a tissue preserving agent;
connecting elements for gas-tightly mating or coupling the vessel to the tissue storage container;
fluid transferring element for causing a transfer of the volume of preserving agent from the vessel to the tissue storage container, when the vessel is gas-tightly mated or coupled to the tissue storage container.

The vessel may include the features described above with reference to the systems of the first and third aspects of the invention as well as the features described above with reference to the method of the second aspect of the invention.

The vessel may hence comprise a compartment for storing the preserving agent, wherein the compartment is closed by a liquid and gas tight closure, said closure being releasable when the vessel is mated or coupled to the tissue storage container. The vessel may be comprised in a lid for closing the tissue storage container.

From the above description, it will be appreciated that embodiments of the various aspects of the present invention provide a comprehensive tissue sampling system that solves the above-mentioned and other problems by comprising the following:

A. A biopsy device comprising an invasive unit with tissue-receiving and tissue-severing components that is capable of harvesting and bringing to a point outside the body of a patient one or more tissue samples.

B. A tissue collecting device that may be brought in detachable operative engagement with the tissue-receiving components of the biopsy device to remove the at least one tissue sample. Said tissue collecting device may optionally comprise one or more tissue chambers for temporary storage of tissue samples during a biopsy procedure. If more than one chamber is available, said chambers may sequentially move or be moved into operative engagement with the tissue-receiving components to collect and individually store tissue samples. By suitable configuration of the tissue collecting device, the sequence and spatial orientation of the acquired tissue samples may be maintained at all times and tissue samples may be supported and protected while they are temporarily held in the tissue collecting device.

C. A tissue storage container that is configured receive either the one or more tissue samples, the entire tissue collecting device or the part of the collecting device that contains the one or more tissue samples. The tissue storage container is furthermore configured to receive a volume of preserving agent while comprising a sealed receptacle that provides a substantially sealed enclosure for the gaseous and liquid phases of the preserving agent.

D. A vessel containing the preserving agent that may be gas-tightly mated or coupled to the tissue storage container and inject the preserving agent into the tissue storage container. Said vessel should preferably contain an amount of preserving agent that is sufficient to cover the at least one tissue sample that is housed in the tissue storage container.

In a particular embodiment, the invention provides a comprehensive tissue sampling system comprising:

A. A multiple biopsy device comprising an invasive unit with tissue-receiving and tissue-severing components that is capable of harvesting and bringing to a point outside the body of a patient a plurality of individual tissue samples in a single device insertion.

B. An automatic tissue collecting device that is in detachable operative engagement with the multiple biopsy device. Said tissue collecting device comprises a housing and a collecting unit that comprises a plurality of individual tissue chambers and is held in the housing by means of a collecting unit lid that is releasably attached to the housing. Said tissue collecting device is capable of sequentially removing from the tissue-receiving components of the biopsy device a plurality of individual tissue samples as they are excised from the body of the patient and of temporarily storing these tissue samples in individual tissue chambers while maintaining at all times the spatial orientation of said samples relative to their positions at the point of sampling. Following completion of a biopsy procedure, the tissue collecting device may be detached from the biopsy device and the collecting unit along with the lid may be removed from the housing and transferred to a tissue storage container while still containing the samples. Thus, physical manipulation of individual samples is avoided.

C. A tissue storage container that is configured to receive the collecting unit of the tissue collecting device and to house said collecting unit along with the samples that are stored in the tissue chambers of the collecting unit. The tissue storage container comprises a receptacle that may be air-tightly mated to a tissue storage container lid and is configured to receive and support the collecting unit. The capacity of the receptacle is dimensioned to ensure that sufficient preserving agent is available to provide proper fixation of the individual samples. The tissue storage container lid may be configured to mate with the lid of the collecting unit, permitting the operator to remove the collecting unit from the housing by holding the tissue storage container lid and the housing, thus avoiding physical manipulation of individual tissue samples.

Furthermore, the tissue storage container lid may be configured to act as a reservoir for a preserving agent and comprises a fully enclosed cavity as well as means for gas-tight mating or coupling to a vessel containing a preserving agent. Suitable configuration of said vessel will provide gas-tight ingress and subsequent controlled egress of said preserving agent into the receptacle. Such means of controlled egress may be configured to provide a user-activated gas- and fluid-tight seal between the storage container lid and the receptacle. Such a seal may be activated subsequent to the egress of the preserving agent from the tissue storage container lid, efficiently limiting the volume of preserving agent needed to adequately cover the samples by keeping the preserving agent contained in the receptacle. Thus, if the amount of preserving agent applied prior to activation matches the capacity of the receptacle, and if the tissue storage container is suitably oriented during egress, it is ensured that the samples will be adequately covered while they are kept in the tissue storage container. If the means of ingress are furthermore configured to act as a gas-tight seal following removal of the vessel, substantially all the air and vapors of preserving agent that is contained in the storage container lid subsequent to the egress of said agent may be encapsulated in said lid. Thus, if ingress and subsequent egress of the agent is done subsequent to attachment of the tissue storage container lid to the receptacle, the lid may act as an air lock, permitting the ingress of the preserving agent into the tissue storage container while at the same time preventing vapors of said agent from escaping from said container to the surrounding environment. By suitable configuration of the user-activated seal, the air and preserving agent that is thus contained may remain encapsulated in the tissue storage container lid even after the lid is removed from the receptacle.

D. A vessel containing formalin or similar preserving agent that is configured as a syringe and may be detachably and air-tightly mated to the ingress means of the lid of the tissue storage container. Said syringe may comprise means for injecting the formalin at a pressure exceeding the atmospheric pressure. This capability is desired since injection of the preserving agent is done into a gas-tightly sealed container that is filled with air at atmospheric pressure prior to injection. As the preserving agent is injected into the storage container, the air in said container is compressed in correspondence with the volume of preserving agent injected. If the tissue storage container is placed with the receptacle in a lower position relative to the tissue storage container lid during injection, and the preserving agent is in a fluid phase, the laws of gravity will cause the preserving agent to move towards the bottom of the receptacle while the air that fills the container will be urged toward the top of the lid. If the capacity of the tissue storage container lid is sufficient or the amount of preserving agent is minimal compared with the amount of air, the operator should have to expend an absolute minimum of force while injecting the preserving agent. Alternatively, suitably configured tools may be provided to assist the operator.

An important advantage of the comprehensive biopsy system according to preferred embodiments of the invention is that it provides extensive protection of the operator from liquid or gaseous components of potentially toxic and/or carcinogenic preserving agents by maintaining for the duration of the procedure all such agents in gas-tight enclosures. As an additional benefit associated with preferred embodiments of such a system, the operator is provided with means of transferring one or more tissue samples from a biopsy device to a preserving agent without having to physically manipulate individual tissue samples. Thus, operator exposure to bio-hazards and bio-contaminants is to a large extent avoided.

According to one embodiment, the ingress means for the preserving agent comprise a female luer lock that is operatively connected to a one-way valve, where the one-way valve is configured to permit the passage of formalin into the container lid while at the same time preventing the escape of air and vapors of preserving agent once the syringe has been removed from airtight connection with the ingress means of the storage container lid.

The egress means comprise a rubber membrane that is an integral part of the container lid. Said rubber membrane features a number of holes. A plastic disc is a removable part of the receptacle and has an equal number of holes that may be brought into alignment with the holes in the rubber membrane. When the storage container lid is placed on the receptacle, the plastic disc is brought to abut and contact the rubber membrane. Alignment of the holes in the rubber membrane and the plastic disc may be done by twisting or rotating the storage container lid to a first locking position. In said first locking position, the storage container lid is air-tightly mated with the receptacle, and formalin may pass from the reservoir that is comprised in the storage container lid to the receptacle to fully cover the tissue samples that are placed in said receptacle.

When the storage container lid is subsequently twisted to a second locking position, airtight mating is maintained while the holes in the rubber membrane are twisted out of alignment with the holes in the plastic disc. Furthermore, the plastic disc is fixedly abutted to the storage container lid and is locked in place resting against—and providing support to—the rubber membrane. In the second locked position, the rubber membrane and the plastic disc thus co-act to provide an airtight and fluid-tight barrier between the formalin that is held in the receptacle and the air that is held in the storage container lid.

Such a separation is advantageous, provided that the receptacle is substantially filled with the preserving agent when the seal is activated, as it ensures that the tissue samples are covered by the preserving agent, e.g. formalin, independent of the orientation of the tissue storage container during transport or other handling since the receptacle will be completely filled.

Yet another advantage with the present system is that the collecting unit, the housing and the tissue storage container may be given unique and identical numbers, bar-codes or similar means of identification—prominently displayed to improve traceability and minimize the risk that tissue samples from one patient are mistakenly mixed up with tissue samples from another patient.

A further advantage of a tissue storage container of such a configuration is that the preserving agent and all vapors of said agent are maintained in airtight enclosures. In some of the envisioned embodiments, such vapors may be kept fully enclosed in the storage container lid until disposal—even after the lid is separated from the receptacle. Further, if opening of the tissue storage container is only done in a pathologist lab or similar facility characterized by the availability of adequate suction/ventilation and other protective equipment, operator exposure should be strongly reduced or entirely eliminated.

In one particular embodiment, the receptacle comprises a net that may enclose the collecting unit and is configured to hold the samples in place in their individual chambers to ensure that they maintain at all times their spatial orientation while at the same time permitting the preserving agent to diffuse into the tissue samples for proper fixation.

In a variant of this embodiment, the net comprises a plastic frame with a threaded section that is configured to mate with locking pins in the lid of the collecting unit.

In one particular variant, the net is removably positioned in the center of the opening of the receptacle and mating takes place when the storage container lid is twisted to its first position. When the storage container lid is subsequently twisted to its second, locked position, the net is twisted along with the lid, maintaining the connection. When the storage container lid is subsequently removed from the receptacle, the net stays attached to the lid of the collecting unit, ensuring that the tissue samples maintain their mutual spatial orientation until the net is removed by a pathologist or similarly trained individual. This feature is particularly advantageous in the harvesting of tissue samples in the prostate, where samples are harvested according to specific systems or methodologies. Since the absence or presence of prostate cancer in specific samples may ultimately determine the choice of treatment, the preserving the order and spatial orientation of the individual samples is crucial.

In an alternative embodiment, the lid of the tissue storage container is pre-filled with the preserving agent and the plastic disc is an integral part of the storage container lid. This permits the elimination of the separate vessel and provides a more user-friendly alternative to the system described above.

Additional aspects of the invention will be apparent to those of ordinary skill in the art in view of the detailed description of various embodiments, which is made with reference to the drawings, a brief description of which is provided below.

DETAILED DESCRIPTION OF THE DRAWINGS

Figure 1:
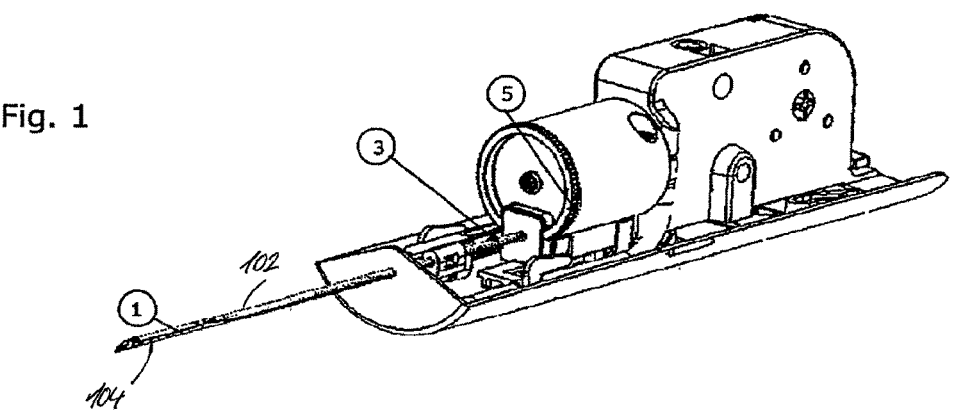
FIG. 1 is a semi-frontal view of a disposable unit according to an aspect of the present invention.
Figure 2:
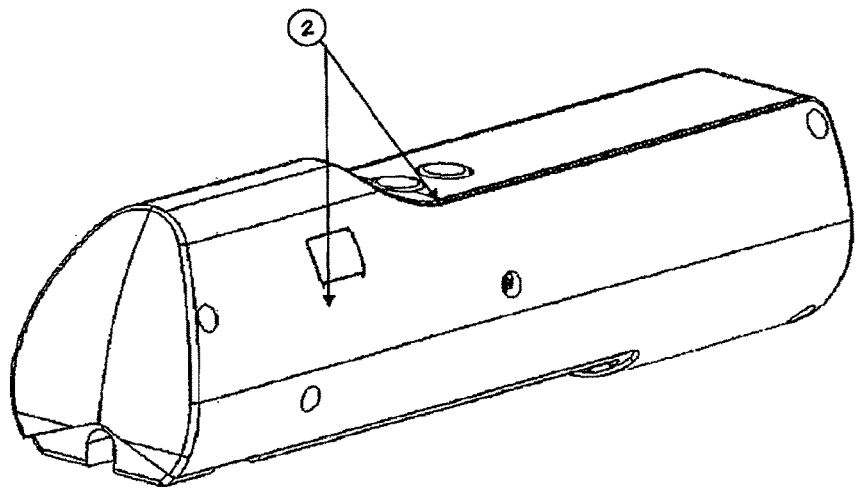
FIG. 2 is a semi-frontal view of a hand-piece according to an aspect of the present invention.

FIGS. 1 and 2 show a multiple biopsy device that is particularly well suited to form part of a comprehensive tissue sampling system in accordance with the invention. The biopsy device comprises a disposable unit with invasive components 1, comprising a cutting cannula 102 and a tissue-receiving container 104 that is movably received in an inner lumen of the cutting cannula 102 in response to the motions of a toothed rack that is attached to the proximal end of said tissue-receiving container, the toothed rack being in turn driven by a motor (not shown).

The biopsy device may include embodiments of the device claimed and described in International Patent Application No. PCT/DK2007/000166, which is hereby incorporated by reference.

Operatively coupled to this disposable unit is a handpiece, shown in FIG. 2. The hand piece includes a power source, a vacuum unit, a motorized driver unit and a user interface 2 comprising twin buttons and a means for visually inspecting a tissue sample at a suitable point in time. By comprising these and other components, said device provides a fully automated tissue harvesting mechanism that is capable of sequentially harvesting multiple tissue samples and bringing these to a point outside the body of a patient.

Furthermore, the device comprises an automatic tissue collecting device 3 (FIG. 1), at least part of which is in operative engagement with the disposable unit. Said tissue collecting device may comprise a collecting unit 4 (FIG. 3) that is stepwise rotatable about a central axis and is detachably received in a housing 5 (FIG. 1).

Figure 3:
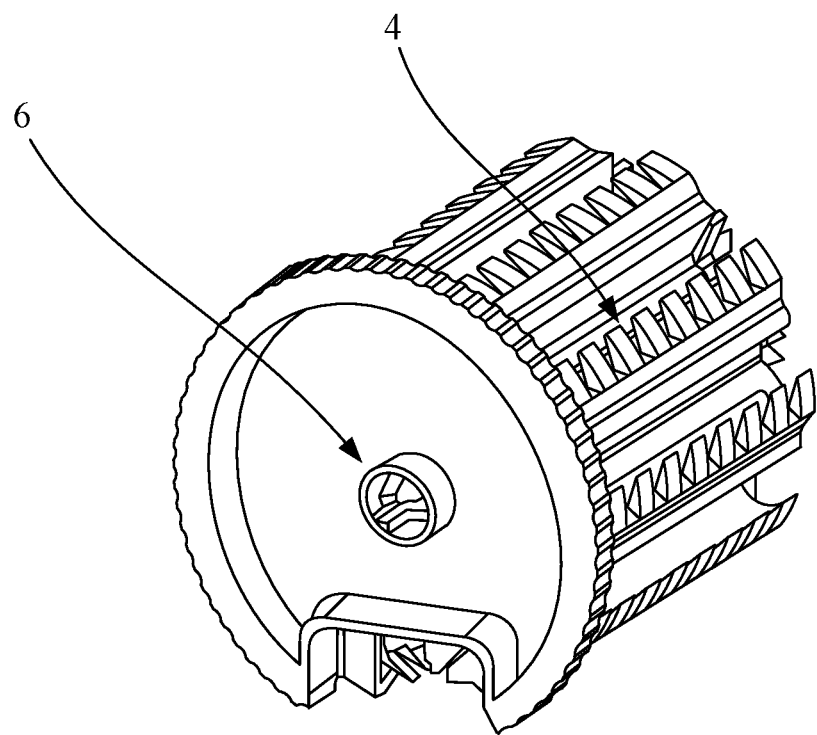
FIG. 3 is a more detailed view of the collecting unit and the collecting unit lid. For clarity, the housing has been removed.
Figure 4:
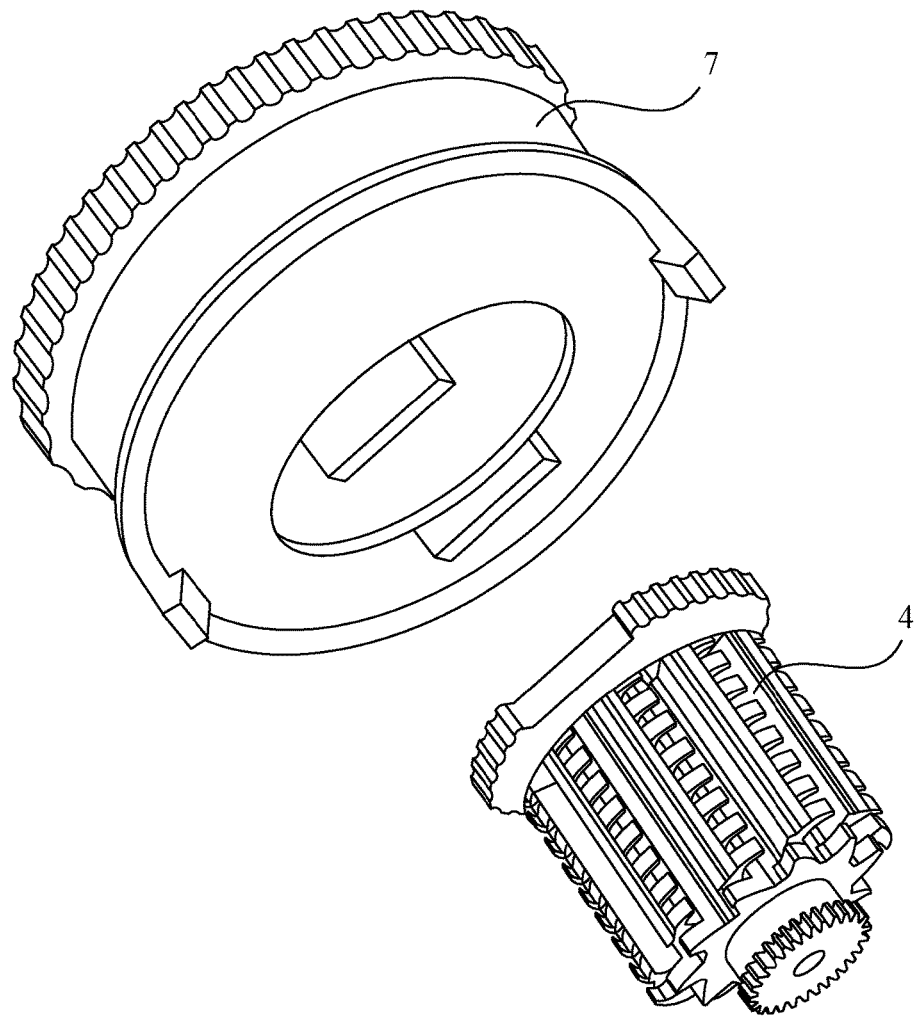
FIG. 4 is an exploded view of the collecting unit with the housing removed as it is being mated to the lid of a tissue storage container.
Figure 5:
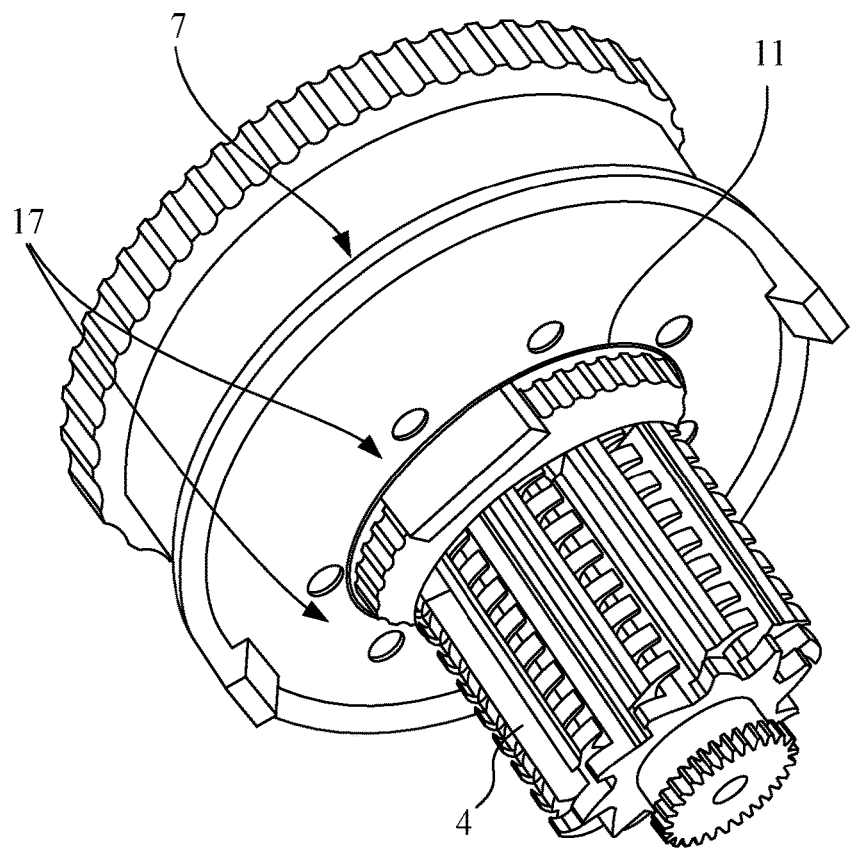
FIG. 5 is an upward-looking view of the collecting unit after being mated to the lid of a tissue storage container.

As shown in FIG. 3, a lid 6 is attached to the collecting unit and is configured to releasably interface with the housing to hold the collecting unit in place in the housing for the duration of a biopsy procedure. The lid is furthermore configured to mate with a tissue storage container lid 7 (FIG. 5), according to a tissue transfer procedure from temporary storage to permanent storage, as shown in FIGS. 4 and 5.

Figure 6:
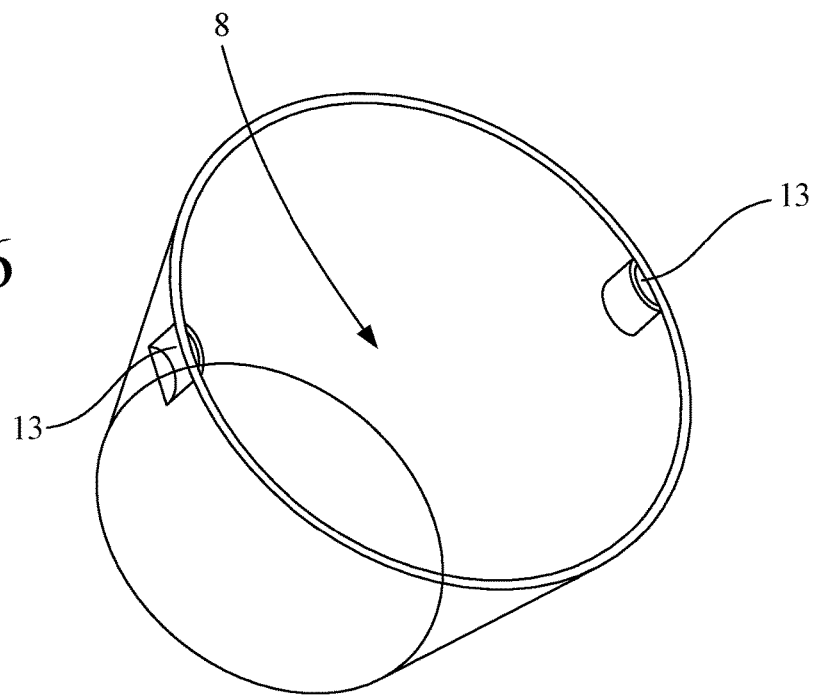
FIG. 6 shows a simple receptacle of a tissue storage container, the receptacle being primarily configured to receive larger tissue samples such as those produced by an open biopsy.
Figure 7:
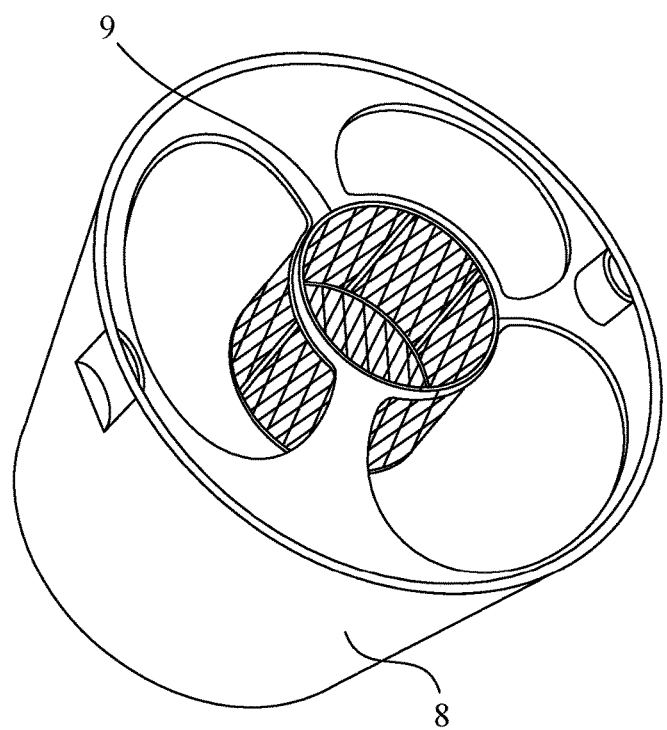
FIG. 7 shows a receptacle of a tissue storage container, the receptacle being more specifically suited to applications with multiple biopsy devices with a net that is configured to enclose the collecting unit of a tissue collecting device.
Figure 8:
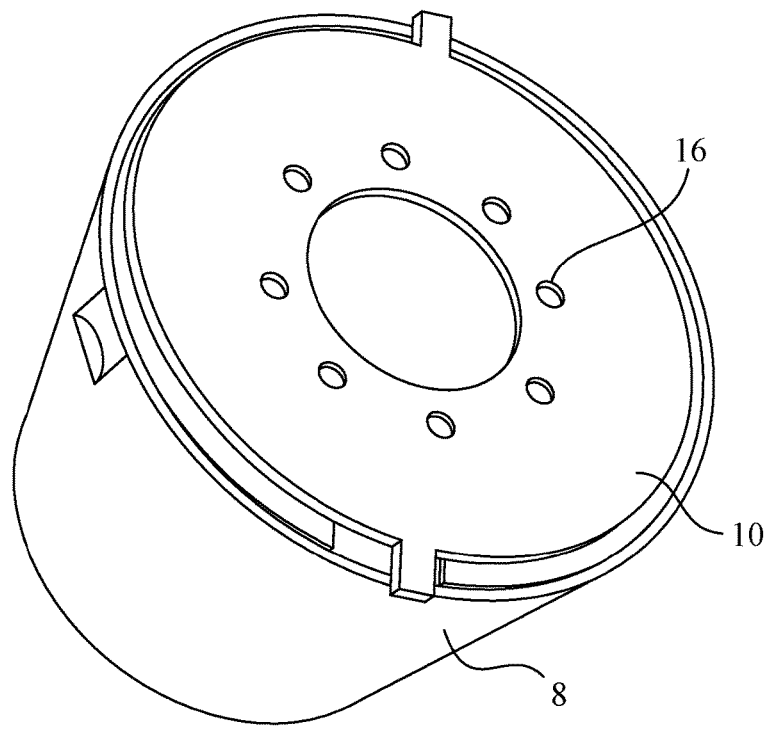
FIG. 8 shows a receptacle for a tissue storage container similar to the receptacles disclosed in FIGS. 6 and 7, with a plastic lid that is a part of a user-activated seal.

FIGS. 6-8 show different receptacles of tissue storage containers for biopsy samples.

FIG. 6 shows a receptacle of a tissue storage container, the receptacle being primarily suited to larger tissue samples that may be placed directly in a trough 8, such as those harvested in an open biopsy. A plastic disc that may form part of a user-activated seal has been omitted from the drawing for the sake of simplicity. However, it should be understood that such a disc may be needed to provide a gas-tight enclosure at all times. It is envisaged that such a receptacle, coupled to a tissue storage container lid, will provide general surgeons with, for example, an advantageous means of protecting themselves against excessive exposure to preserving agents, such as formalin, while handling the tissue samples.

Figure 9:
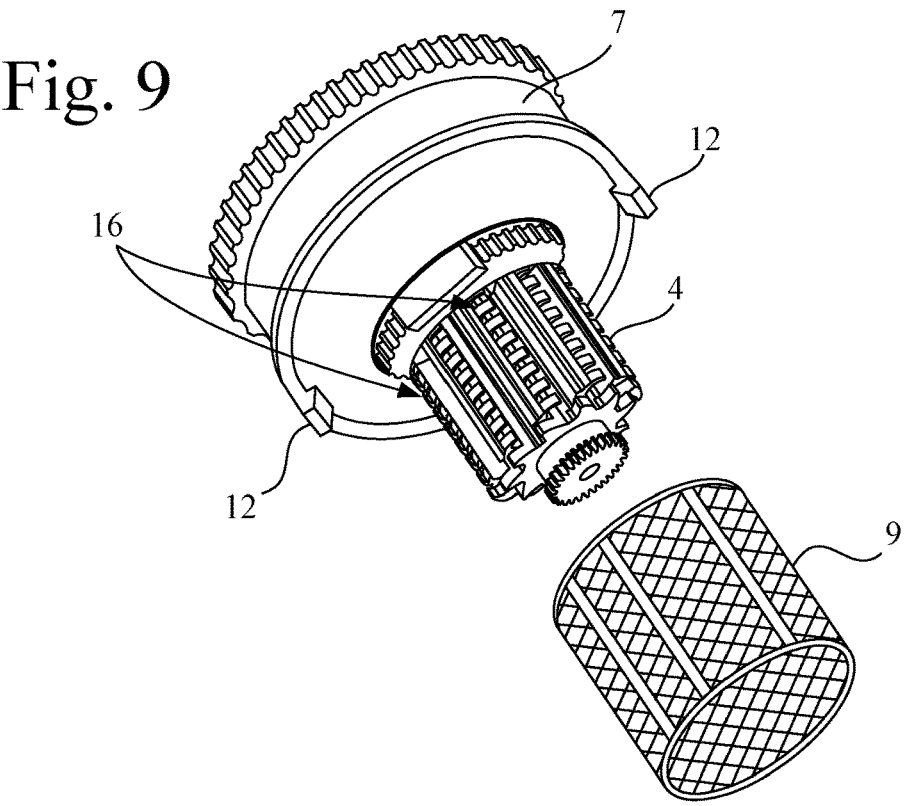
FIG. 9 is an upward-looking view of the collecting unit as it is inserted into the net that is comprised in one particular embodiment of the receptacle of the tissue storage container. For clarity, the tissue storage container with its receptacle is omitted from this figure.
Figure 10:
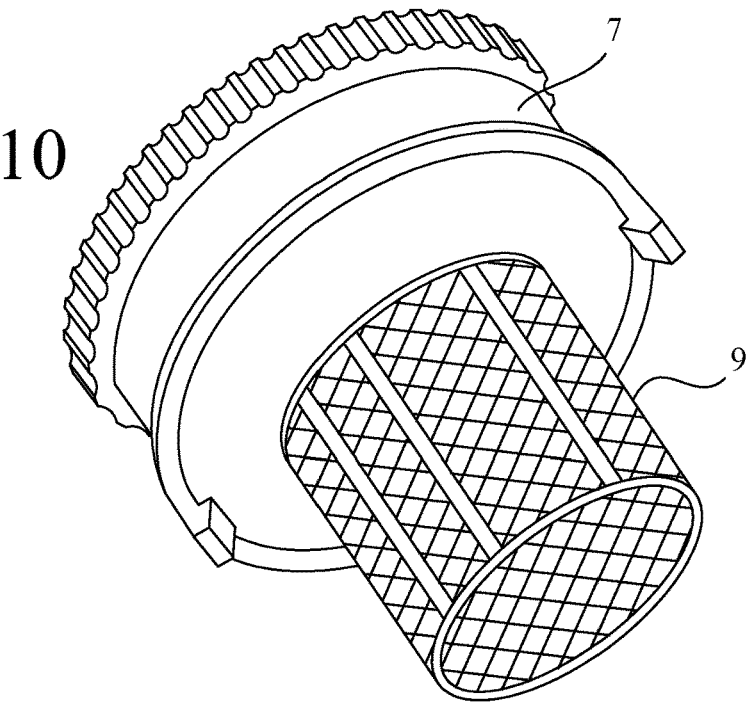
FIG. 10 is an upward-looking view of the collecting unit after being inserted into and firmly attached to the net described in FIG. 6.

FIG. 7 shows a receptacle of a tissue storage container, the receptacle being configured to interface with multiple biopsy devices such as the one shown in FIGS. 1 and 2. The receptacle comprises a net 9 that is removably suspended centrally over the trough 8 and is configured to receive and enclose a collecting unit of the biopsy device. Said net may comprise a supporting frame of plastic or similar material with structure for releasably mating with the lid of the collecting unit. Such structure may for instance comprise two or more locking grooves that are formed in the frame and are configured to receive two or more locking pins that are formed in the collecting unit lid. Such a net is thought to be of particular relevance in the sampling of lesions in the prostate, where the sequence and orientation of tissue samples relative to their origin in the sampled tissue is crucial. For such applications, it is important to ensure that the tissue samples—or fragments of these—do not drift away from the tissue chambers where they were originally placed. The net should therefore be comprised of a very fine mesh. FIGS. 9 and 10 show the collecting unit 4 and the net 9 before and after mating. For the sake of simplicity, the tissue storage container with its receptacle is omitted.

In addition to the above, the net 9 may also be used to house a plurality of individual tissue samples, such as those harvested with a conventional core needle or a multiple biopsy device without a tissue collecting device. Such samples may either be placed directly in the net, or they may be kept separate. This may, for instance, be accomplished by providing a net that is or may be divided into smaller compartments. This may be accomplished by inserting suitably configured partitions that are supported by the plastic frame, for example.

FIG. 8 shows a receptacle of a tissue storage container, the receptacle being similar to the receptacle of FIGS. 6 and 7, but according to this variant, a plastic disc 10 is removably placed over the trough 8 of the receptacle. Said plastic disc 10 comprises a plurality of holes 16 that may be aligned with a similar plurality of holes 17 in a rubber membrane 11 to provide a fluid path (FIG. 5). The membrane is an integral part of the tissue storage container lid. These two components may be combined to comprise a gas and fluid tight seal between the tissue storage container lid and the trough 8 of the receptacle. In a particular embodiment, the combination is accomplished by mating the plastic disc 10 with the tissue storage container lid by means of at least two essentially rectangular locking bars 12 (FIG. 9). The bars 12 are formed in the outer periphery of the plastic disc 10 and are configured to slide in at least two recesses 13 in the rim of the receptacle (FIG. 6). The length of these recesses determines the free rotating motion that the plastic disc may perform relative to the receptacle. Said locking bars may be brought in operative engagement with at least two locking recesses (not shown). Said locking recesses are formed in the rim of the tissue storage container lid as said lid is twisted towards its second locked position. When this is done, the plastic disc 10 is held stationary relative to the twisting motion of the tissue storage lid, and the holes 17 in the rubber membrane 11 are twisted out of alignment with the holes 16 in the plastic disc 10. In this position, the rubber membrane 11 and the plastic disc 10 comprise a user-activated seal that is gas-and fluid-tight and may provide a barrier between the tissue storage container lid and the trough 8 of the receptacle, independent of the shape or size of said receptacle.

Figure 11:
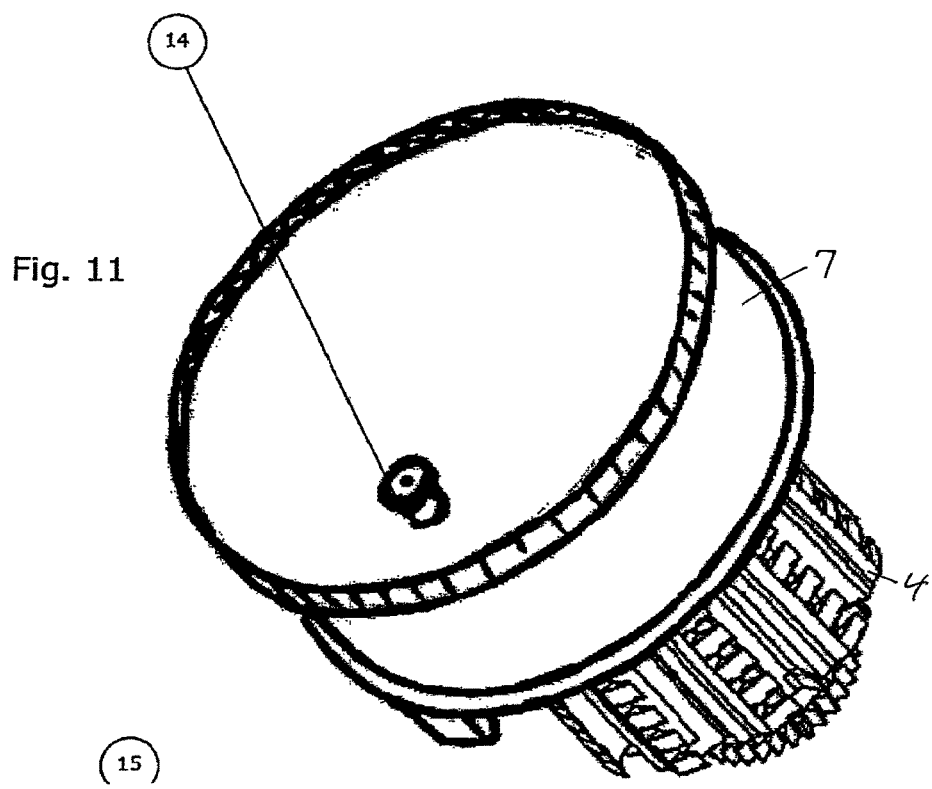
FIG. 11 shows a tissue storage container lid comprising a luer lock with an operatively connected one-way valve that is configured to receive a syringe. In one embodiment of this invention, the syringe is used to inject formalin into the tissue storage lid, wherefrom it passes into the receptacle of the tissue storage container to cover the tissue samples that are housed in the tissue collecting unit.
Figure 12:
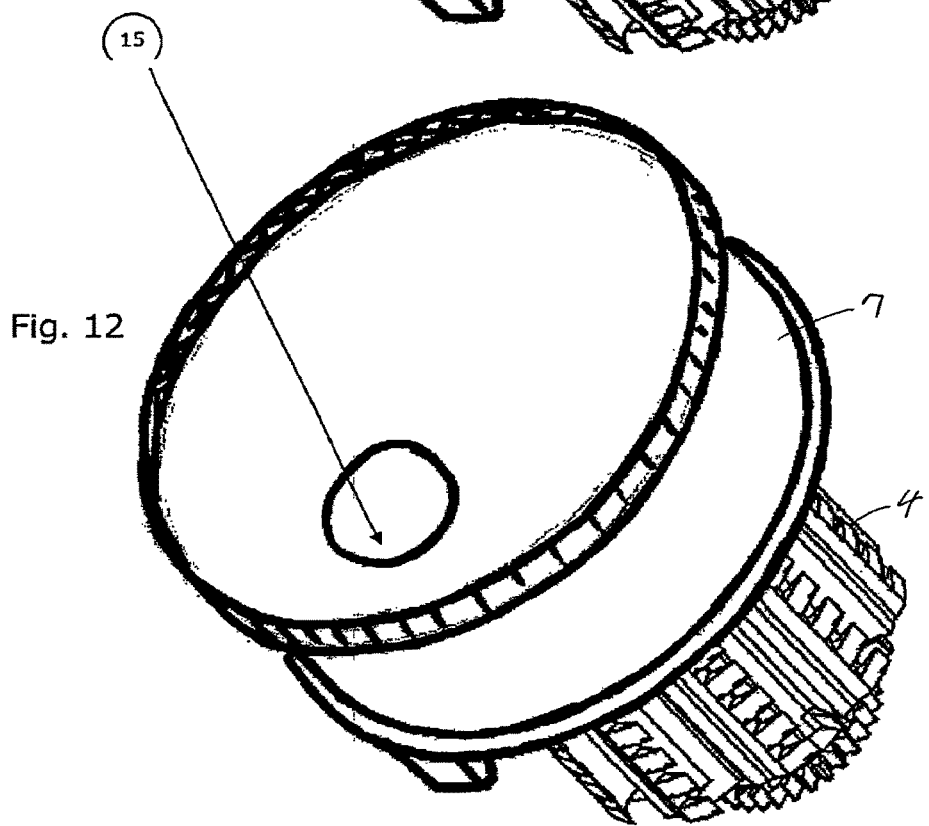
FIG. 12 shows a tissue storage container lid similar to that of FIG. 11, but with a septum instead of a luer lock.

FIGS. 11 and 12 show specific ingress means in accordance with specific embodiments of the present invention.

FIG. 11 shows a tissue storage lid that comprises a female luer lock 14 in operative connection with a one-way valve (not shown). Said luer lock is configured to receive a syringe containing a preserving agent (e.g., formalin) and to provide a gas-tight seal for the duration of injection of the preserving agent, as well as following removal of the syringe.

FIG. 12 shows an alternative embodiment that comprises a rubber septum 15 that may be pierced, for instance, by a hypodermic needle that is coupled to a syringe.

In the following, a particular embodiment of a comprehensive tissue sampling system is used for explanatory purposes, but it is understood that the principles and methods disclosed in this invention are not restricted to usage with this particular system.

When a biopsy is prescribed, the operator may prepare a biopsy device in accordance with the instructions for use for that particular device. The exemplary device that is a part of the comprehensive tissue sampling system is prepared by removing a protective foil from the transport container of a sterile disposable unit and subsequently removing the disposable unit from a transport container therefor.

While maintaining sterility, the operator may then insert and couple the sterile disposable unit to a hand-piece. Coupling energizes the device. The operator may then proceed to carry out a desired number of biopsies in accordance with the instructions for use and the principles of procedure that pertain to that particular type of biopsies, as described e.g. in International Patent Application No. PCT/DK2007/000166, which is hereby incorporated by reference.

During a biopsy procedure carried out with the exemplary device, tissue samples are sequentially harvested and placed in a tissue-receiving container. Said tissue-receiving container is then transported to a point outside the body of the patient that corresponds with an automatic tissue-collecting device.

Said tissue-collecting device is a part of the disposable unit. It comprises means for ejecting a plurality of sequentially arriving tissue sample from the tissue-receiving container and of temporarily storing said plurality of tissue samples in individual tissue chambers. In one particular embodiment, the ejection means comprise a comb-like ejector frame with a plurality of ejector pins. Said ejector pins are temporarily insertable through a plurality of holes in the tissue-receiving container, which is capable of reciprocating motion relative to the tissue-receiving container. The means for temporarily storing a plurality of tissue samples may comprise a cylindrical, drum-like collecting unit with a number of semi-open tissue chambers distributed evenly along—and sunk into—its circumference. A plurality of lands and grooves configured to interface with the ejector pins of the ejector frame are also distributed along the circumference and perpendicular to an axis of rotation. Said collecting unit is movably housed in a housing that is releasably attached to the remainder of the disposable unit, and is stepwise rotatable about a central axle to sequentially expose each of a plurality of tissue chambers to receive a tissue sample. A collecting unit lid is configured to releasably hold the collecting unit in place in the housing by providing at least one locking pin releasably received in at least one locking recess in the inner periphery of the housing.

When a tissue sample has been harvested and transported to a point corresponding with the automatic tissue-collecting device, said device is energized by means comprised in the hand-piece. The ejector frame is moved from a first lowered position towards a second raised position, through which movement the plurality of ejector pins are brought in contact with the tissue sample that recedes in the tissue-receiving container. Said contact urges the tissue sample out of the tissue-receiving container and into the exposed opening of one of a plurality of semi-open tissue chambers. Subsequent to this, the collecting unit starts rotating, whereby the lands and grooves of the collecting unit mesh with the fully raised ejector pins. By suitably configuring the points of interception of the grooves and lands with the tissue chambers, fork-like structures may be obtained that may gently support and lift the tissue sample off the ejector pins as these begin their motion towards their first lowered position.

The fork-like structure is shown in FIG. 3. Thus, the tissue-receiving chamber may be emptied without requiring the intervention of an operator, and the tissue-receiving container may be repositioned in the anatomy of the patient to receive another tissue sample.

By repeating the above procedure a desired number of times, a desired number of biopsy samples may be harvested in a single device insertion.

Such and other embodiments of tissue harvesting and collecting systems are described further in International Patent Application No. PCT/DK2007/000166, which is hereby incorporated by reference.

Figure 13:
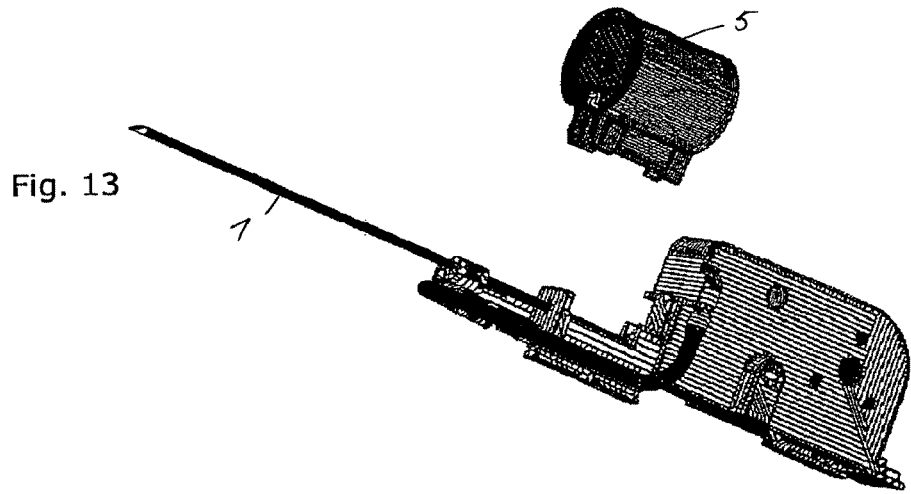
FIGS. 13-20 show the operating sequence of the transfer of tissue samples from the temporary storage of a tissue collecting device to the more permanent storage and fixation according to a specific embodiment of the present invention.

Subsequent to the harvesting of the desired number of biopsy samples, the device may be removed from the anatomy of the patient. By decoupling the disposable unit from the hand-piece, access to the tissue-collecting device may be obtained. Subsequently, the housing—along with the collecting unit and the collecting unit lid—may be detached from the disposable unit, as shown in FIG. 13.

A significant advantage of the invention is to permit the operator to apply to the tissue samples a volume of a preserving agent such as formalin while at the same time protecting the operator from exposure to said preserving agent.

Another advantage is to allow the operator to transfer the tissue samples from the temporary storage that is provided by the tissue-collecting device to a more permanent storage where fixation of samples is possible without having to physically manipulate individual samples.

In the particular embodiment of the comprehensive tissue sampling system, these and other problems are solved by providing a tissue storage container that comprises an essentially gas-tight enclosure when closed and has a lid that may be mated to the collecting unit lid with a snap-lock.

Figure 14:
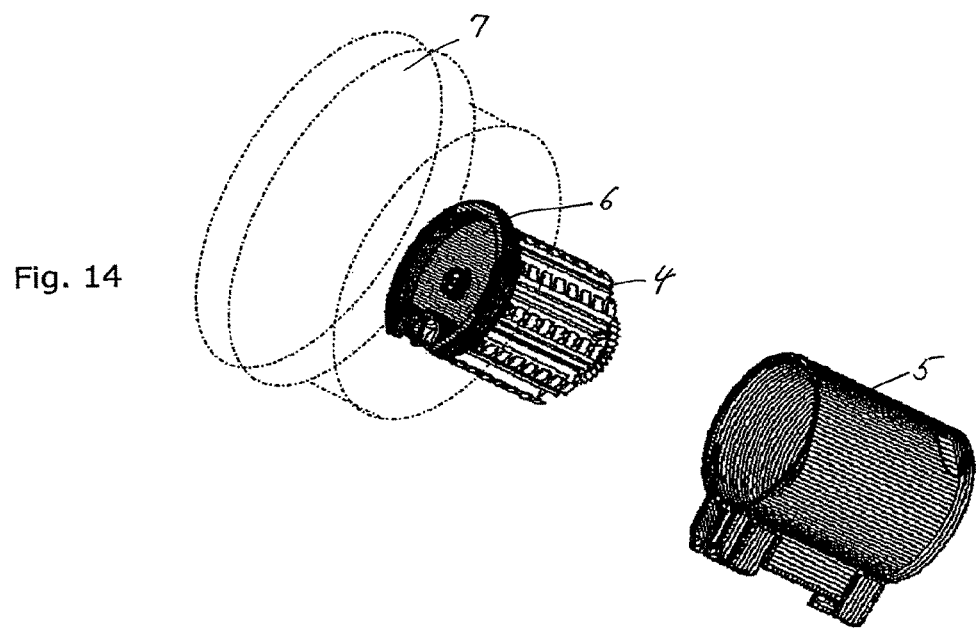
Figure 15:
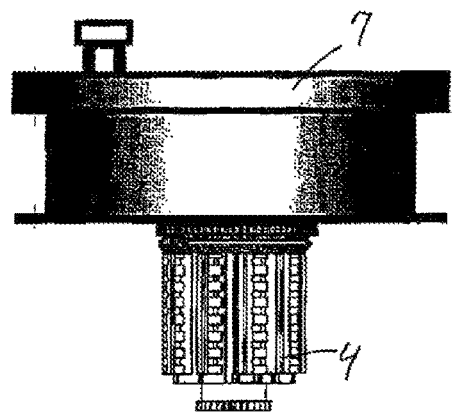

When the operator has detached the housing 5—along with the collecting unit 4 and the collecting unit lid 6—from the disposable unit, he may attach the storage container lid 7 to the collecting unit lid 6 by means of twin locking pins that are configured to mate with twin locking recesses in the collecting unit lid 6. By twisting the tissue storage container lid in a counterclockwise direction, he may unscrew the collecting unit lid 6 from the housing 5. The collecting unit 4 along with the samples may then be removed from the housing 5, as shown in FIG. 14. FIG. 15 shows the collecting unit 4 mated to the tissue storage container lid 7.

Figure 16:
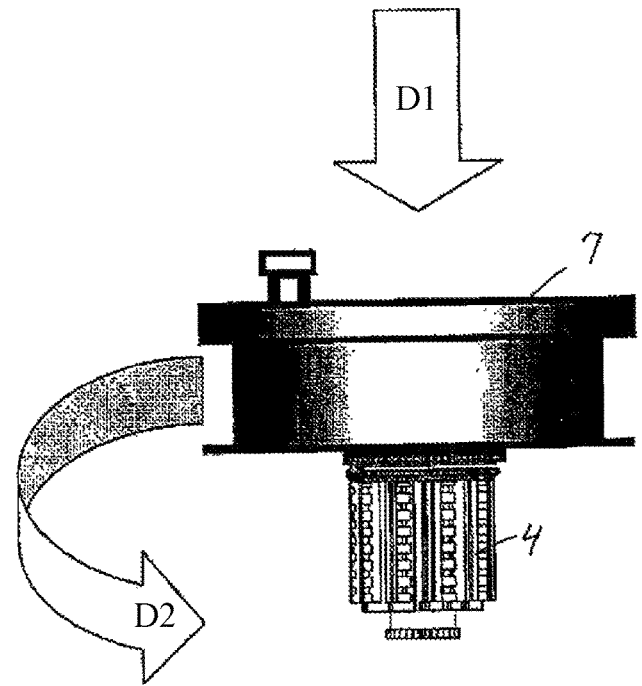
Figure 16:
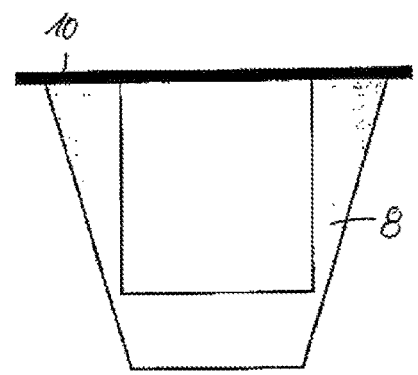

Subsequent to removal of the housing 5, the rim of the tissue storage container lid 7 may be placed against the rim of the receptacle of the tissue storage container while the collecting unit 4 is inserted in the central hole of a plastic disc 10 that is removably placed over the trough of the receptacle and is a part of a user-activated seal between the tissue storage container lid and the receptacle, as shown in FIG. 16. The arrow denominated "D1" shows the direction of insertion of the collecting unit through the hole in the plastic disc 10. Immediately behind the plastic disc—and suspended centrally above the trough 8 of the receptacle—is placed a net that is configured to receive and enclose the collecting unit as well as the tissue samples that are held in their individual tissue chambers.

To securely join the tissue storage container lid 7 and the receptacle 8, the operator may then twist the lid to a first locked position, as shown by the arrow denominated "D2". In this position, properly configured seals of rubber or a similar material ensure that the tissue storage container remains a gas-tight enclosure as soon as the tissue storage container lid has been twisted into said first locking position.

In addition, at least two locking pins in the collecting unit lid 7 are screwed into a threading in the rim of the net as the tissue storage container lid is twisted into its first locking position, ensuring that the net remains attached to the collecting unit to keep the samples in place in the tissue chambers.

Figure 17:
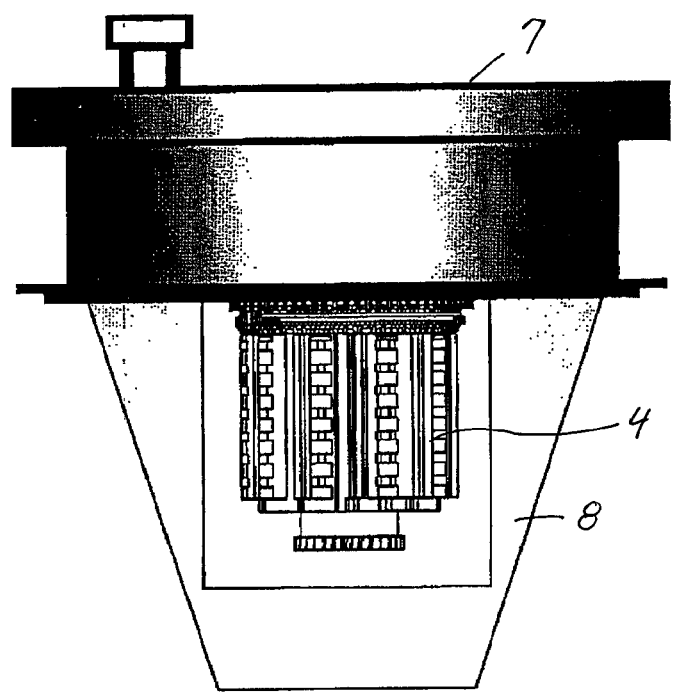

As the tissue storage container lid 7 is twisted to the first locked position, a plurality of holes in the plastic plate is aligned with a similar plurality of holes in a rubber membrane that comprises another part of a user-activated seal between the tissue storage container lid and the receptacle. Thus, a fluid connection is established between the reservoir in the tissue storage container lid 7 and the receptacle 8. FIG. 17 shows the tissue storage container fully assembled and awaiting the ingress of the preserving agent.

Figure 18:
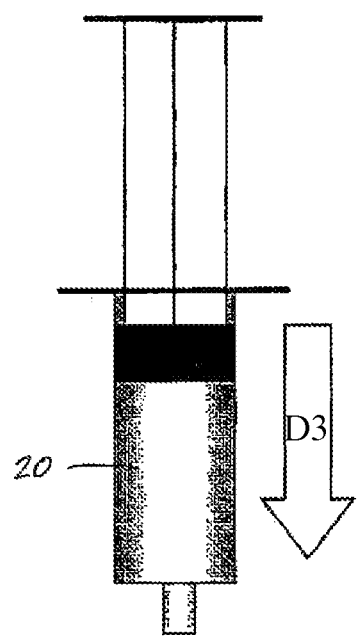
Figure 18:
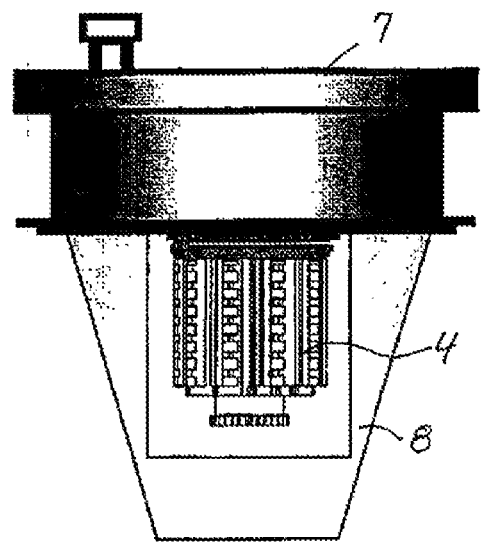

The first locked position of the tissue storage container lid corresponds with the ingress stage. Accordingly, the operator may mate or connect a vessel 20 containing a preserving agent to the tissue storage container lid, as shown in FIG. 18. The arrow denominated "D3" shows the direction of connection of the vessel 20.

In one particular embodiment, connection is accomplished by screwing a syringe containing formalin onto a female luer lock that is in operative connection with a one-way valve, but other means of gas-tight connection between a vessel and an ingress means are also envisioned, such as a hypodermic needle that is inserted in a septum or a hose with a clamp that is pressed onto a spout.

Figure 19:
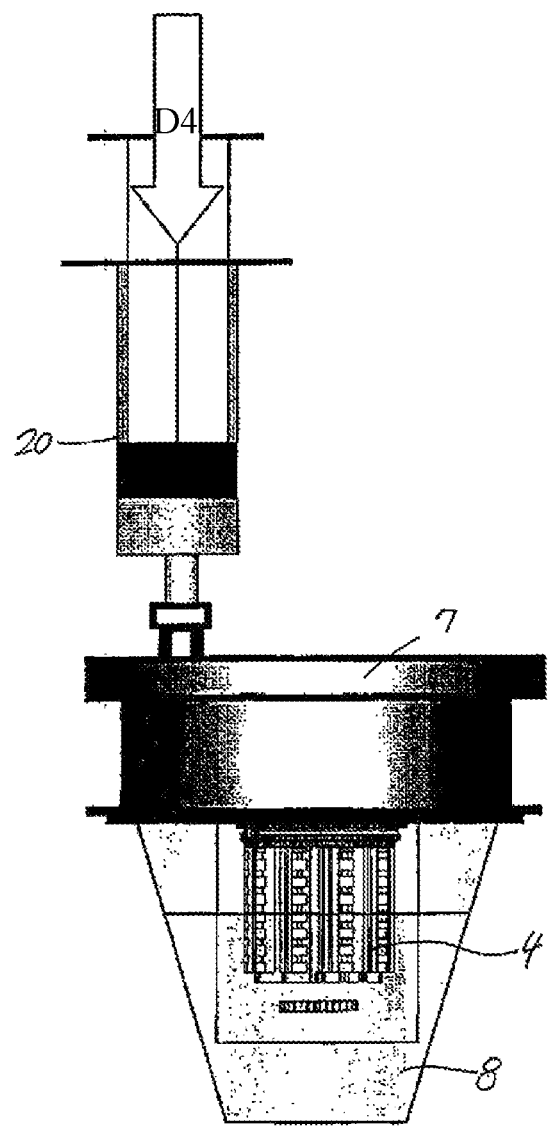

Once a gas-tight connection has been accomplished, the operator may place the tissue storage container including the receptacle 8 and the lid 7 on a horizontal surface with the bottom of the receptacle resting on said surface, and inject the contents of the vessel 20 (i.e. syringe) into the reservoir that is comprised in the tissue storage container lid. Injection is shown in FIG. 19, with the arrow denominated "D4" showing the direction of motion of the syringe plunger.

The holes that are comprised in the rubber membrane and the plastic disc will permit the preserving agent to run from the reservoir into the receptacle, while at the same time permitting air from the receptacle to flow into the tissue storage lid.

Following completion of the injection, the operator may remove the syringe from its gas-tight connection with the tissue storage container lid. In accordance with the present embodiment, the one-way valve operatively connected to the female luer lock will prevent the escape of compressed air and vapors of preserving agent.

Figure 20:
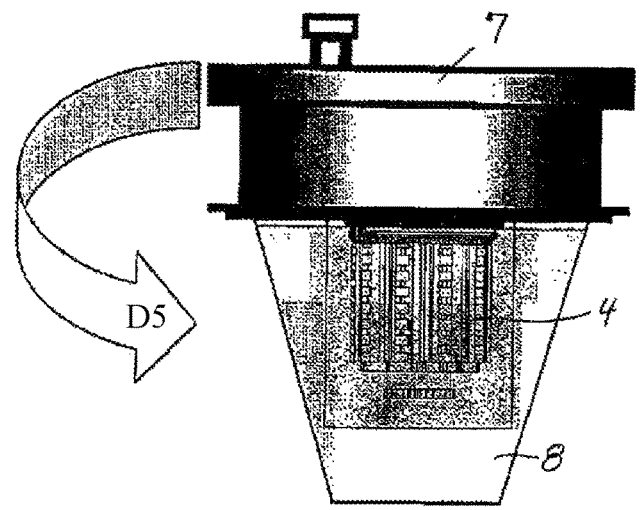

Subsequent to removal of the syringe, the operator may operate the user-activated seal by twisting the tissue storage container lid to its second locked position, as shown in FIG. 20. The arrow denominated "D5" shows the direction of twisting. During this, the plastic disc is held stationary by at least two ridges that are formed in the rim of the receptacle and are brought to rest against at least two locking bars that are formed in the plastic disc. The rubber membrane, meanwhile, twists along with the tissue storage container lid, which causes the holes in the membrane to rotate out of alignment with the holes in the plastic disc. The combination of the inherent stiffness of the membrane material and the pressure exerted by the compressed air contained in the reservoir of the tissue storage container lid will ensure that the rubber membrane is held against the plastic disc to provide a fluid-tight seal, effectively keeping the preserving agent contained in the receptacle during transport.

While the tissue storage container lid is twisted towards its second locked position, the at least two locking bars of the plastic disc slide into operative engagement with at least two locking recesses formed in the rim of the tissue storage container lid 7. By suitable configuration of the locking bars and/or the locking recesses (e.g., by forming snap locks in either one or the other), the plastic disc may be mated to the tissue storage container lid. Since the plastic disc is removably placed over the trough 8 of the receptacle, it will stay attached to the tissue storage container lid when the lid is removed, pressing at all times against the rubber membrane to maintain the fluid-tight seal.

When the tissue storage container lid has been twisted to its second closed position, the tissue storage container along with the tissue samples may be sent to the pathologist for further analysis.

When the pathologist desires to further evaluate the tissue samples, he should position the tissue storage container in a fume closet before removing the tissue storage container lid from the receptacle. While the compressed air and vapors of preserving agent should be gas-tightly contained within the tissue storage container lid by the user-activated seal, a little compressed air will most likely be trapped between the surface of the preserving agent and the seal. Furthermore, some preserving agent is bound to escape in gaseous form while the receptacle is open.

The pathologist should therefore leave the receptacle in the fume closet while removing the net from the collecting unit and samples from the collecting unit tissue chambers, whereupon he may reseal the receptacle by replacing the tissue storage container lid.

It is understood that such a tissue storage system may also be adapted to function with other types of biopsy devices than the described multiple biopsy device. For instance, the individual tissue cores that are produced by conventional core needle devices may be placed on millipore paper, for example, which in turn may be placed either in the main compartment of the receptacle or in the net of the receptacle. This will permit the operator to inject the preserving agent without exposure to the preserving agent.

Figure 21:
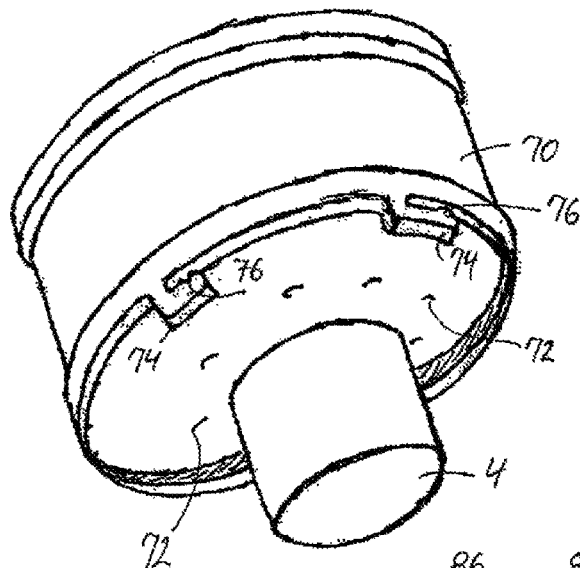
FIGS. 21-24 illustrate an embodiment of a tissue storage container, the lid of which itself constitutes a vessel for containing a preserving agent.
Figure 21:
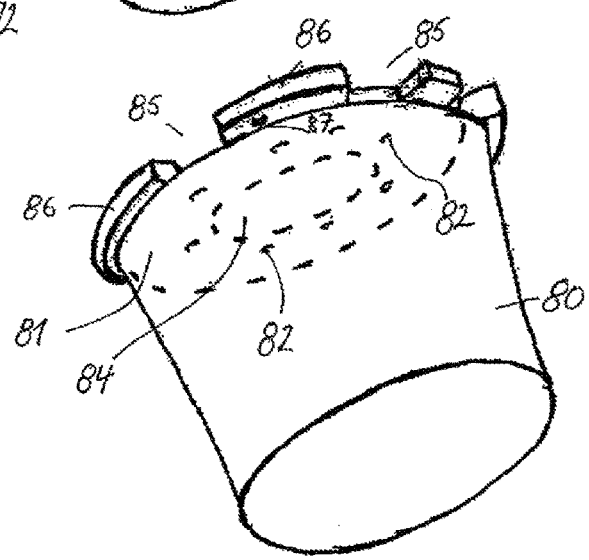

FIGS. 21-24 illustrate an embodiment of a tissue storage container, the lid of which itself constitutes a vessel for a preserving agent. As shown in FIG. 21, the tissue storage container comprises a receptacle 80 for receiving the collecting unit 4 attached to a tissue storage container lid 70. The lid contains a volume of a tissue preserving agent, such as formalin. The receptacle is partially covered by a disc 81 having a central opening 84 for receiving the collecting unit 4. The disc also includes holes 82 for receiving a volume of preserving agent released through apertures 72 provided in a lower portion of the lid 70, as described below. The apertures may optionally be closed or sealed. L-shaped projections 74 are provided on a rim portion of the tissue storage container lid 70. Upon axial displacement of the collecting unit 4 into the receptacle 4, the L-shaped projections 74 pass through interstices 85 formed in a rim portion 86 of the receptacle 80. Depressions 76 in the L-shaped projections may subsequently engage protrusions 87 in the rim portion 86 of the receptacle 80, as described further below.

Figure 22:
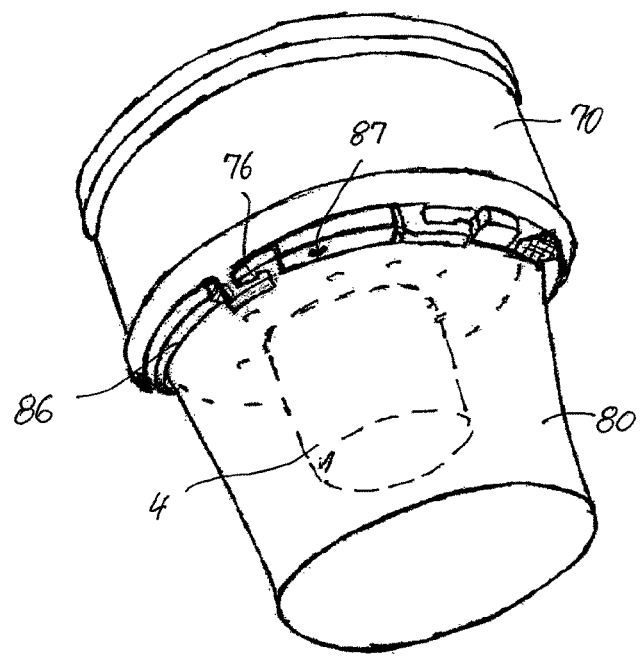
Figure 23:
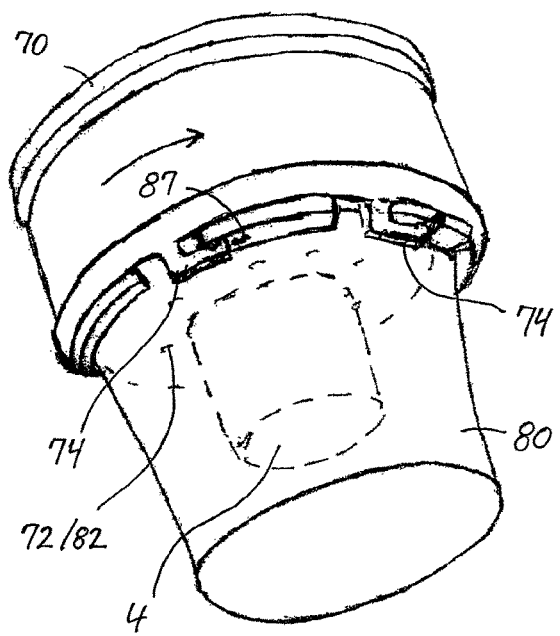

In the state shown in FIG. 22, the tissue storage container lid 70 has been placed so that its lower rim portion abuts the rim portion 86 of the receptacle 80, with the collecting unit 4 placed in a trough of the receptacle 80. The lid 70 may then be twisted to the position shown in FIG. 23, i.e. to a first locked position, in which the holes 82 formed in the disc 81 of the receptacle 80 are aligned with the apertures 72 formed in the lower portion of the lid 70. As a consequence of twisting of the lid 70 to the position shown in FIG. 23, seals optionally closing the apertures 72 may be broken, e.g. ruptured by suitable rupturing structure provided e.g. on an upper surface of the disc 81. The volume of preserving agent in the lid 70 is then allowed to flow into the receptacle 80. Preferably, the volume of preserving agent in the lid 70 is just sufficient to fill the receptacle 80 to entirely cover the tissue sample(s) held by the collecting unit 4.

Figure 24:
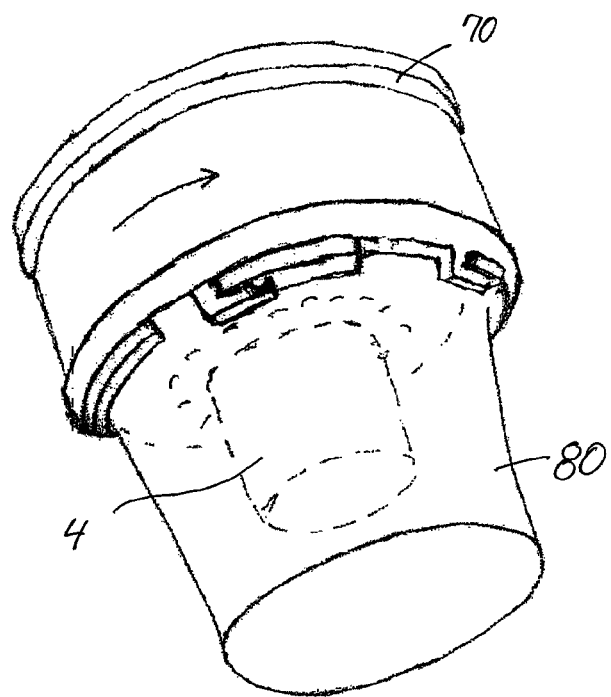

Finally, the lid 70 is twisted further as shown in FIG. 24 to a second locked position, in which the depressions 76 in the L-shaped projections 74 are engaged by the projections 87 of the rim portions 86 of the receptacle 80. In the second locked position, the apertures 72 are rotated beyond the holes 82 and hence fully covered by material of the disc 81, so that the preserving agent now contained in the vessel 80 is prevented from flowing back into the lid 70.

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

The invention claimed is:

1. A tissue handling system, comprising:
 a biopsy device configured to deliver at least one tissue sample to a location outside the body of a patient;
 a tissue storage container separate from the biopsy device; and
 a tissue collecting device configured to releasably engage the biopsy device to receive the at least one tissue sample from the biopsy device, the tissue collecting device configured to be disengaged from the biopsy device and engaged with the tissue storage container to deliver the at least one tissue sample to the tissue storage container,
 wherein the biopsy device comprises a disposable unit, the disposable unit configured for operative engagement with the tissue collecting device, and wherein the tissue collecting device is rotatably mounted to the disposable unit for stepwise rotation about a central axis, the tissue collecting device having a plurality of tissue chambers.

2. The tissue handling system of claim 1, wherein the tissue storage container is configured to receive the entire tissue collecting device after the tissue collecting device is disengaged from the disposable unit.

3. A tissue handling system, comprising:
a biopsy device configured to deliver at least one tissue sample to a location outside the body of a patient;
a tissue storage container separate from the biopsy device;
a tissue collecting device configured to releasably engage the biopsy device to receive the at least one tissue sample from the biopsy device, the tissue collecting device configured to be disengaged from the biopsy device and engaged with the tissue storage container to deliver the at least one tissue sample to the tissue storage container; and
a vessel containing a preserving agent for delivery into the tissue storage container.

4. The tissue handling system of claim 3, comprising a receptacle in selective fluid communication with the vessel, and wherein the preserving agent is released from the vessel into the receptacle when the tissue collecting device is mounted to the tissue storage container.

5. The tissue handling system of claim 3, wherein the tissue storage container has a receptacle, the preserving agent being released into the receptacle as a consequence of the connecting of the tissue collecting device to the tissue storage container.

6. A tissue handling system, comprising:
a biopsy device that includes a disposable unit having invasive components;
a tissue collecting device removably mountable to the disposable unit; and
a tissue storage container separate from the biopsy device and the tissue collecting device, the tissue storage container configured to removably mount the tissue collecting device after the tissue collecting device is removed from the biopsy device,
wherein the tissue collecting device has a collecting unit and an interface lid connected to the collecting unit, the interface lid configured to be sequentially connected to each of the biopsy device and the tissue storage container, the collecting unit having at least one chamber configured to receive a tissue sample from the biopsy device and configured to deliver the tissue sample to the tissue storage container.

7. A method of using a tissue handling system, comprising:
providing a biopsy device configured to deliver at least one tissue sample to a location outside the body of a patient;
providing a tissue storage container separate from the biopsy device;
providing a tissue collecting device configured to releasably engage each of the biopsy device and the tissue storage container;
engaging the tissue collecting device with the biopsy device to receive the at least one tissue sample from the biopsy device;
disengaging the tissue collecting device from the biopsy device; and
engaging the tissue collecting device with the tissue storage container to deliver the at least one tissue sample to the tissue storage container.

8. The method of claim 7, comprising providing the biopsy device with a disposable unit, the disposable unit configured for operative engagement with the tissue collecting device.

9. The method of claim 8, comprising rotatably mounting the tissue collecting device to the disposable unit for stepwise rotation about a central axis, the tissue collecting device having a plurality of tissue chambers.

10. The method of claim 9, comprising receiving the entire tissue collecting device in the tissue storage container after the tissue collecting device is disengaged from the disposable unit.

11. The method of claim 7, comprising:
providing a vessel containing a preserving agent; and
delivering the preserving agent into the tissue storage container.

12. The method of claim 7, comprising:
providing the tissue storage container with a vessel containing a preserving agent and a receptacle in selective fluid communication with the vessel; and
releasing the preserving agent from the vessel into the receptacle when the tissue collecting device is mounted to the tissue storage container.

13. The method of claim 7, comprising:
providing the tissue storage container with a receptacle; and
releasing a preserving agent into the receptacle as a consequence of the connecting of the tissue collecting device to the tissue storage container.

* * * * *